US012729194B2

(12) United States Patent
Smith, III et al.

(10) Patent No.: US 12,729,194 B2
(45) Date of Patent: Sep. 8, 2026

(54) COMPOUNDS FOR THE TREATMENT OF HUMAN IMMUNODEFICIENCY VIRUS

(71) Applicants: THE TRUSTEES OF THE UNIVERSITY OF PENNSYLVANIA, Philadelphia, PA (US); DANA-FARBER CANCER INSTITUTE, INC., Boston, MA (US)

(72) Inventors: Amos B. Smith, III, Merion, PA (US); Althea Erica Gaffney, Alexandria, VA (US); Joseph G. Sodroski, Medford, MA (US)

(73) Assignees: THE TRUSTEES OF THE UNIVERSITY OF PENNSYLVANIA, Philadelphia, PA (US); DANA-FARBER CANCER INSTITUTE, Boston, MA (US)

( * ) Notice: Subject to any disclaimer, the term of this patent is extended or adjusted under 35 U.S.C. 154(b) by 952 days.

(21) Appl. No.: 17/765,983

(22) PCT Filed: Oct. 1, 2020

(86) PCT No.: PCT/US2020/053675
§ 371 (c)(1),
(2) Date: Apr. 1, 2022

(87) PCT Pub. No.: WO2021/067528
PCT Pub. Date: Apr. 8, 2021

(65) Prior Publication Data

US 2022/0402899 A1 Dec. 22, 2022

Related U.S. Application Data

(60) Provisional application No. 62/908,985, filed on Oct. 1, 2019.

(51) Int. Cl.

| | |
|---|---|
| ***C07D 405/14*** | (2006.01) |
| ***A61K 39/00*** | (2006.01) |
| ***A61P 31/18*** | (2006.01) |
| ***C07D 209/20*** | (2006.01) |
| ***C07D 403/12*** | (2006.01) |
| ***C07D 405/04*** | (2006.01) |

(52) U.S. Cl.
CPC ............ *C07D 405/14* (2013.01); *A61K 39/00* (2013.01); *A61P 31/18* (2018.01); *C07D 209/20* (2013.01); *C07D 403/12* (2013.01); *C07D 405/04* (2013.01)

(58) Field of Classification Search
CPC ............................ C07D 405/14; C07D 403/12
See application file for complete search history.

(56) References Cited

U.S. PATENT DOCUMENTS

| | | | |
|---|---|---|---|
| 2003/0069245 | A1 | 4/2003 | Wallace et al. |
| 2004/0162298 | A1 | 8/2004 | Ho et al. |
| 2012/0276141 | A1 | 11/2012 | Srivastava et al. |

FOREIGN PATENT DOCUMENTS

| | | | |
|---|---|---|---|
| WO | 02/04440 | A1 | 1/2002 |
| WO | 2012/019003 | A1 | 2/2012 |

OTHER PUBLICATIONS

Alkhatib et al., "CC CKR5: a RANTES, MIP-1alpha, MIP-1beta receptor as a fusion cofactor for macrophage-tropic HIV-1", Science, 1996, 272, 1955-1958.

Alsahafi et al., "An asymmetric opening of HIV-1 envelope mediates antibody-dependent cellular cytotoxicity", Cell Host Microbe, 2019, 25, 578-587.

Andrabi et al., "Identification of common features in prototype broadly neutralizing antibodies to HIV envelope V2 apex to facilitate vaccine design", Immunity, 2015, 43, 959-973.

Blattner et al., "Structural delineation of a quaternary, cleavage-dependent epitope at the gp41-gp120 interface on intact HIV-1 Env trimers", Immunity, 2014, 40, 669-680.

Castillo-Menendez et al., "Comparison of uncleaved and mature human immunodeficiency virus membrane envelope glycoprotein trimers", J Virol., 2018, 92, e00277-18.

(Continued)

*Primary Examiner* — Shawquia Jackson
(74) *Attorney, Agent, or Firm* — BakerHostetler

(57) ABSTRACT

The present disclosure provides compounds of Formula (I) or pharmaceutically acceptable salts thereof: (I) wherein, R1 to R6 and X are defined herein. Also provided are pharmaceutical compositions comprising these compounds, methods for treating Human Immunodeficiency Virus (HIV-1) in a subject in need thereof using these compounds or pharmaceutical compositions, and methods for stabilizing the state-1 conformation of the HIV-1 envelope glycoproteins using these compounds or pharmaceutical compositions.

(I)

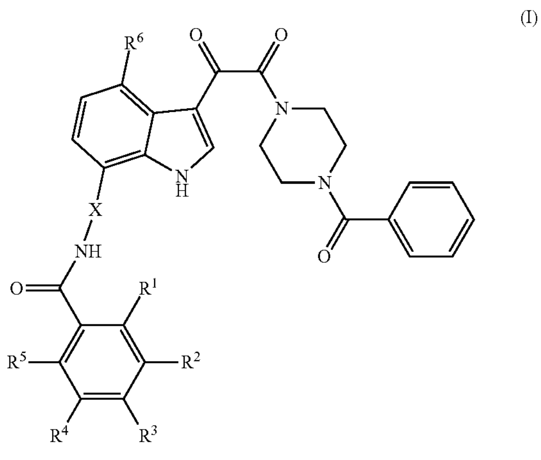

26 Claims, 15 Drawing Sheets

(56) References Cited

OTHER PUBLICATIONS

Castillo-Menendez et al., "Conformational differences between functional human immunodeficiency virus envelope glycoprotein trimers and stabilized soluble trimers", J Virol., 2019, 93, e01709-18.
Chakrabarti et al., "Direct antibody access to the HIV-1 membrane-proximal external region positively correlates with neutralization sensitivity", J Virol., 2011, 85, 8217-8226.
Chakrabarti et al., "HIV type 1 Env precursor cleavage state affects recognition by both neutralizing and nonneutralizing gp41 antibodies", AIDS Res Hum Retroviruses, 2011, 27, 877-887.
Chan et al., "Core structure of gp41 from the HIV envelope glycoprotein", Cell, 1997, 89, 263-273.
Dalgleish et al., "The CD4 (T4) antigen is an essential component of the receptor for the AIDS retrovirus", Nature, 1984, 312, 763-767.
Feng et al., "HIV-1 entry cofactor: functional cDNA cloning of a seven-transmembrane, G protein-coupled receptor", Science, 1996, 272, 872-877.
Gray et al., "Antibody specificities associated with neutralization breadth in plasma from human immunodeficiency virus type 1 subtype C-infected blood donors", J. Virol., 2009, 83, 8925-8937.
Gray et al., "The neutralization breadth of HIV-1 develops incrementally over four years and is associated with CD4+ T cell decline and high viral load during acute infection", J Virol., 2011, 85, 4828-4840.
Guo et al., "Biochemical and genetic characterizations of a novel human immunodeficiency virus type 1 inhibitor that blocks gp120-CD4 interactions", J Virol., 2003, 77, 10528-10536.
Haim et al., "Proteolytic processing of the human immunodeficiency virus envelope glycoprotein precursor decreases conformational flexibility", J. Virol., 2013, 87, 1884-1889.
Herschhom et al., "A broad HIV-1 inhibitor blocks envelope glycoprotein transitions critical for entry", Nat Chem Biol., 2014, 10, 845-852.
Herschhom et al., "Release of gp120 restraints leads to an entry-competent intermediate state of the HIV-1 envelope glycoproteins", MBio 7, 2016, e01598-16.
Herschhom et al., "The beta20-beta21 of gp120 is a regulatory switch for HIV-1 Env conformational transitions", Nat Commun., 2017, 8, 1049.
Ho et al., "Envelope conformational changes induced by human immunodeficiency virus type 1 attachment inhibitors prevent CD4 binding and downstream entry events", J Virol., 2006, 80, 4017-4025.
Hraber et al., "Prevalence of broadly neutralizing antibody responses during chronic HIV-1 infection", AIDS, 2014, 28, 163-169.
Huang et al., "Broad and potent HIV-1 neutralization by a human antibody that binds the gp41-gp120 interface", Nature, 2014, 515, 138-142.
Juette et al., "Single-molecule imaging of non-equilibrium molecular ensembles on the millisecond timescale", Nat Methods, 2016, 13, 341-344.
Kassa et al., "Transitions to and from the CD4-bound conformation are modulated by a single-residue change in the human immunodeficiency virus type 1 gp120 inner domain", J Virol., 2009, 83, 8364-8378.
Klatzmann et al., "T-lymphocyte T4 molecule behaves as the receptor for human retrovirus LAV", Nature, 1984, 312, 767-768.
Kowalski et al., "Functional regions of the envelope glycoprotein of human immunodeficiency virus type 1", Science, 1987, 237, 1351-1355.
Labrijn et al., "Access of antibody molecules to the conserved coreceptor binding site on glycoprotein gp120 is sterically restricted on primary human immunodeficiency virus type 1", J Virol., 2003, 77, 10557-10565.
Lalezari et al., "Safety and efficacy of the HIV-1 attachment inhibitor prodrug BMS-663068 in treatment-experienced individuals: 24 week results of AI438011, a phase 2b, randomised controlled trial", Lancet, 2015, HIV 2, e427-437.
Lin et al., "A small molecule HIV-1 inhibitor that targets the HIV-1 envelope and inhibits CD4 receptor binding", Proc Natl Acad Sci USA, 2003, 100, 11013-11018.
Liu et al., "Molecular architecture of native HIV-1 gp120 trimers", Nature, 2008, 455, 109-113.
Lu et al., "Associating HIV-1 envelope glycoprotein structures with states on the virus observed by smFRET", Nature, 2019, 568, 415-419.
Ma et al., "HIV-1 Env trimer opens through an asymmetric intermediate in which individual protomers adopt distinct conformations". Elife, 2018, 7, e34271.
Madani et al., "Localized changes in the gp120 envelope glycoprotein confer resistance to human immunodeficiency virus entry inhibitors BMS-806 and #155", J Virol., 2004, 78, 3742-3752.
McKeating et al., "Differential loss of envelope glycoprotein gp120 from virions of human immunodeficiency virus type 1 isolates: effects on infectivity and neutralization", J Virol., 1991, 65, 852-860.
Melikyan et al., "Evidence that the transition of HIV-1 gp41 into a six-helix bundle, not the bundle configuration, induces membrane fusion", J Cell Biol, 2000, 151, 413-423.
Melillo et al., "Small-molecule CD4-mimics: Structure-base optimization of HIV-1 entry inhibition", ACS Med Chem Letters, 2016, 7, 330-334.
Montefiori et al., "Magnitude and breadth of the neutralizing antibody response in the RV144 and Vax003 HIV-1 vaccine efficacy trials", J Infect Dis., 2012, 206, 431-441.
Moore et al., "Dissociation of gp120 from HIV-1 virions induced by soluble CD4", Science 250, 1990, 1139-1142.
Moore et al., "Limited neutralizing antibody specificities drive neutralization escape in early HIV-1 subtype C infection", PLoS Pathog, 2009, 5, e1000598.
Munro et al., "Conformational dynamics of single HIV-1 envelope trimers on the surface of native virions", Science, 2014, 346, 759-763.
Nowicka-Sans et al., "In vitro antiviral characteristics of HIV-1 attachment inhibitor BMS-626529, the active component of the prodrug BMS-663068", Antimicrob Agents Chemother, 2012, 56, 3498-3507.
Ozorowski et al., "Open and closed structures reveal allostery and pliability in the HIV-1 envelope spike", Nature, 2017, 547, 360-363.
Pacheco et al., "Residues in the gp41 ectodomain regulate HIV-1 envelope glycoprotein conformational transitions induced by gp120-directed inhibitors", J Virol., 2017, 91, e02219-16.
Pancera et al., "Crystal structures of trimeric HIV envelope with entry inhibitors BMS-378806 and BMS-626529", Nat Chem Biol, 2017, 13, 1115-1122.
Pancera et al., "Selective recognition of oligomeric HIV-1 primary isolate envelope glycoproteins by potently neutralizing ligands requires efficient precursor cleavage", Virology, 2005, 332, 145-156.
Parker et al., "Illuminating HIV gp120-ligand recognition through computationally-driven optimization of antibody recruiting molecules", Chem Sci., 2014, 5, 2311-2317.
Pauthner et al., "Vaccine-induced protection from homologous Tier 2 SHIV challenge in nonhuman primates depends on serum-neutralizing antibody titers", Immunity, 2019, 50, 241-252 e246.
PubChem CID 68186295, Create Date Nov. 30, 2012, 7 pages.
Sattentau et al., "Conformational changes induced in the human immunodeficiency virus envelope glycoprotein by soluble CD4 binding", J. Exp. Med., 1991, 174, 407-415.
Si et al., "Small-molecule inhibitors of HIV-1 entry block receptor-induced conformational changes in the viral envelope glycoproteins", Proc Natl Acad Sci U S A 101, 5036-5041, 2004.
Tan et al., "Atomic structure of a thermostable subdomain of HIV-1 gp41", Proc. Natl. Acad. Sci USA, 1997, 94, 12303-12308.
Thali et al., "Resistance to neutralization by broadly reactive antibodies to the human immunodeficiency virus type 1 gp120 glycoprotein conferred by a gp41 amino acid change", J Virol., 1994, 68, 674-680.
Torrents de la Pena et al., "Immunogenicity in rabbits of HIV-1 SOSIP trimers from Clades A, B, and C, given individually, sequentially, or in combination", J Virol., 2018, 92.

(56) References Cited

OTHER PUBLICATIONS

Walker et al., "A limited number of antibody specificities mediate broad and potent serum neutralization in selected HIV-1 infected individuals", PLoS Pathog, 2010, 6, e1001028.
Wang et al., "Cryo-EM structure of a CD4-bound open HIV-1 envelope trimer reveals structural rearrangements of the gp120 V1V2 loop", Proc Natl Acad Sci U S A, 2016, 113, E7151-E7158.
Wang et al., "Discovery of 4-benzoyl-1-[(4-methoxy-1H-pyrrolo[2,3-b]pyridin-3-yl)oxoacetyl]-2-(R)-methylpiperazine (BMS-378806): a novel HIV-1 attachment inhibitor that interferes with CD4-gp120 interactions", J Med Chem., 2003, 46, 4236-4239.
Wei et al., "Antibody neutralization and escape by HIV-1", Nature, 2003, 422, 307-312.
Weissenhorn et al., "Atomic structure of the ectodomain from HIV-1 gp41", Nature, 1997, 387, 426-430.
Wilson et al., "The site of an immune-selected point mutation in the transmembrane protein of human immunodeficiency virus type 1 does not constitute the neutralization epitope", J Virol., 1990, 64, 3240-3248.
Wyatt et al., "The HIV-1 envelope glycoproteins: fusogens, antigens, and immunogens", Science, 1998, 280, 1884-1888.
Xiang et al., "Mutagenic stabilization and/or disruption of a CD4-bound state reveals distinct conformations of the human immunodeficiency virus type 1 gp120 envelope glycoprotein", J Virol., 2002, 76, 9888-9899.
Regueiro-Ren et al., "Inhibitors of human immunodeficiency virus type 1 (HIV-1) attachment. 12. Structure-activity relationships associated with 4-fluoro-6-azaindole derivatives leading to the identification of 1-(4-benzoylpiperazin-1-yl)-2-(4-fluoro-7-[1,2,3]triazol-1-yl-1h-pyrrolo[2,3-c]pyridin-3-yl)ethane-1,2-dione (BMS-585248)", Journal of Medicinal Chemistry, vol. 56, 2013, pp. 1656-1669.

COMPOUNDS FOR THE TREATMENT OF HUMAN IMMUNODEFICIENCY VIRUS

CROSS-REFERENCE TO RELATED APPLICATIONS

This application is the National Stage of International Patent Application No. PCT/US2020/053675, filed Oct. 1, 2020, which claims the benefit of U.S. Provisional Patent Application No. 62/908,985, filed Oct. 1, 2019, the contents of which are incorporated by reference herein.

GOVERNMENT RIGHTS

This invention was made with government support under Contract No. GM056550 and A1150471 awarded by the National Institutes of Health. The government has certain rights in the invention.

TECHNICAL FIELD

The disclosure relates to compounds and methods for treating human immunodeficiency virus.

BACKGROUND

The entry of human immunodeficiency virus (HIV-1) into target cells is mediated by envelope glycoprotein (Env) spikes on the viral membrane. HIV-1 Env trimers consist of three gp120 exterior glycoproteins and three gp41 transmembrane glycoproteins. The gp120 subunits of Env bind the target cell receptors, CD4 and either CCR5 or CXCR4. CD4 binding drives Env from its pre-triggered (State-1) conformation to an obligate intermediate (State 2) and then to the full CD4-bound (State-3) conformation. In the State-3 Env, the gp41 heptad repeat (HR1) region is formed and exposed. Subsequently, the hydrophobic fusion peptide at the gp41 N-terminus is thought to interact with the target cell membrane. Binding of gp120 to the CCR5 or CXCR4 chemokine receptor leads to formation of a highly stable gp41 six-helix bundle, in which the HR2 helix near the viral membrane binds in an antiparallel manner to the HR1 coiled coil. The favorable energy change associated with six-helix bundle formation is used to fuse the viral and target cell membranes.

BMS-378806 (BMS-806) is a potent inhibitor of HIV-1 entry. BMS-663068 (Fostemsavir), the prodrug of the potent analogue BMS-626529 (Temsavir; BMS-529), exhibits favorable antiviral and pharmacokinetic properties and is being evaluated as an anti-HIV-1 therapy in clinical trials.

BMS-378806

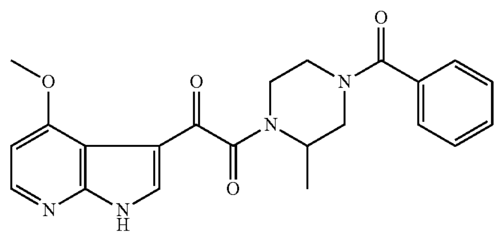

-continued

BMS-663038

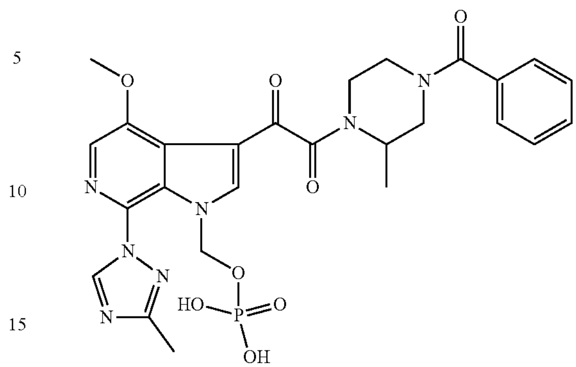

BMS-626529

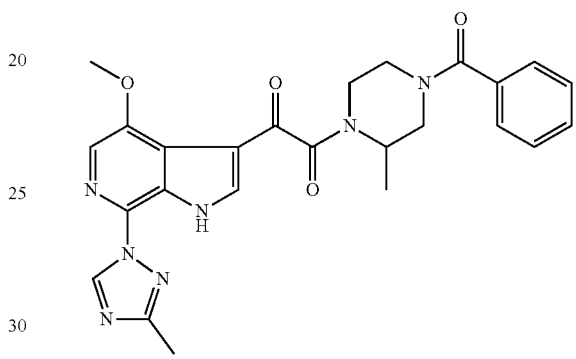

BMS-806, BMS-529 and related HIV-1 entry inhibitors bind gp120 in a hydrophobic pocket located immediately adjacent to the CD4-binding site, between the 020-021 loop and the al helix. At concentrations in the range where potent antiviral effects are seen, the BMS-806 analogues block CD4-induced conformational changes in Env that lead to the formation/exposure of the gp41 HR1 coiled coil. At higher concentrations, BMS-806 can impede CD4 binding. However, BMS-806 inhibits CD4-independent HIV-1 infection as efficiently as CD4-dependent infection, indicating an antiviral mechanism that does not necessarily involve CD4.

During natural HIV-1 infection, antibodies are elicited to many distinct conformations of Env. The majority of these antibodies recognize Env conformations other than State 1; most of these antibodies are sterically blocked from accessing their epitopes after Env engages CD4 on the target cell, and thus have little or no ability to neutralize primary HIV-1 strains; these antibodies are poorly neutralizing antibodies. In a minority of individuals infected by HIV-1 for several years, antibodies capable of neutralizing a wide range of HIV-1 strains are elicited; these antibodies are broadly neutralizing antibodies (bNAbs). Most bNAbs recognize conserved epitopes on the surface of the State-1 Env conformation. Broadly neutralizing antibodies have not been elicited in animals or humans immunized with HIV-1 Env preparations, including stabilized soluble Env trimers.

What is needed are alternate compounds for treating HIV-1.

SUMMARY

The present disclosure provides compounds of Formula (I) or pharmaceutically acceptable salts thereof:

(I)

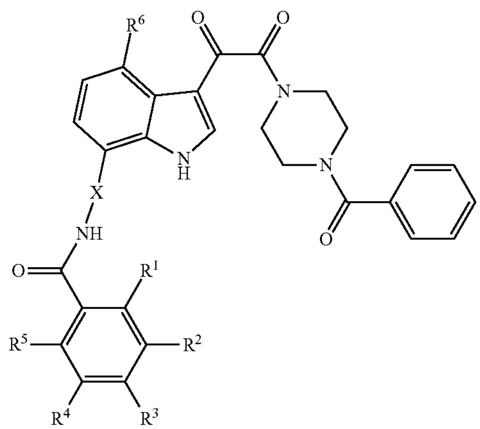

wherein, $R^1$ to $R^6$ are, independently, H, halo, optionally substituted $C_{1-6}$alkyl, optionally substituted diazirinyl, or $N_3$ and X are defined herein.

In some embodiments, the compounds are of formula (IA):

(IA)

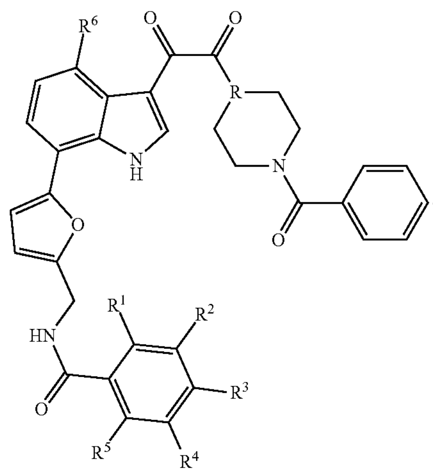

In other embodiments, the compounds are of formula (IB):

(IB)

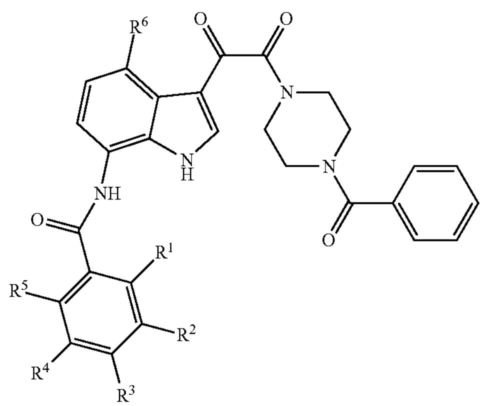

The disclosure also provides pharmaceutical compositions comprising one or more compounds described herein.

The disclosure further provides methods for treating human immunodeficiency virus (HIV) in a subject in need thereof, comprising administering one or more compounds or pharmaceutical compositions described herein to the subject in need thereof. In some embodiments, the HIV is HIV-1.

The disclosure also provides methods for stabilizing the state-1 conformation of the HIV-1 envelope glycoproteins, comprising administering one or more compounds or pharmaceutical compositions described herein to the subject in need thereof.

Other aspects and embodiments of the invention will be readily apparent from the following detailed description of the invention.

BRIEF DESCRIPTION OF THE DRAWINGS

FIG. 1A is a western blot showing A549-Env cells expressing HIV-$1_{AD8}$ Env were incubated with the indicated antibodies, in the absence or presence of 10 μM BMS-806. The cells were then washed and lysed, and cell lysates were incubated with Protein A-Sepharose beads. For the samples with BMS-806, the compound was also added to the cell lysates at a 10 μM concentration. Precipitates were analyzed by Western blotting with a rabbit anti-gp120 antiserum (upper panels) or the 4E10 anti-gp41 antibody (lower panels). The experiment was repeated twice, and a typical result is shown. hIgG—human immunoglobulin G. FIG. 1B is a graph showing precipitation of the gp120 and gp160 glycoproteins was quantified from two independent experiments like that shown in FIG. 1A, and is reported relative to the input level of each glycoprotein. Recognition of the indicated Env glycoprotein by poorly neutralizing antibodies and bNAbs was compared in the absence and presence of BMS-806, using a two-tailed paired Students' t-test. * $P<0.05$; ns—not significant. FIG. 1C is a western blot showing recognition of cell-surface Env by C34-Ig was assessed in the absence or presence of sCD4 and BMS-806. In parallel, recognition of cell-surface Env by CD4-Ig and by a negative control, human IgG (hIgG), was studied.

FIG. 2A is a western blot of VLPs prepared from the supernatants of A549-Gag/Env cells expressing HIV-$1_{AD8}$ Env and Gag-mCherry were solubilized in Triton X-100, and the VLP lysates were incubated with the indicated antibodies. Precipitates were Western blotted with a rabbit anti-gp120 antibody (upper panels) or the 4E10 anti-gp41 antibody (lower panels). FIG. 2B is a graph showing the correlation between the effect of BMS-806 on antibody recognition of gp120 from VLPs solubilized as in a and the effect of BMS-806 on recognition of cell-surface gp120 Env (as in FIG. 1A). In each case, the effect of BMS-806 represents gp120 precipitation by the antibody in the presence of BMS-806 divided by gp120 precipitation in the absence of BMS-806. r, Pearson correlation coefficient. FIG. 2C is a Western blot of VLPs from A549-Gag/Env cell supernatants were incubated with antibodies in the absence or presence of BMS-806 and then pelleted and washed. The repelleted VLPs were solubilized in Triton X-100 and the VLP lysates were incubated with Protein A-Sepharose beads. Precipitates were Western blotted with a rabbit anti-gp120 antibody (upper panels) or the 4E10 anti-gp41 antibody (lower panels). FIG. 2D is a dot plot showing the correlation between the effect of BMS-806 on antibody recognition of gp120 Env on intact, detergent-free VLPs (as in FIG. 3C) and the effect of BMS-806 on recognition of cell-surface gp120 Env (as in FIG. 1A). In each case, the effect of BMS-806 represents the precipitation of gp120 by the antibody in the presence of BMS-806 divided by gp120 precipitation in the absence of BMS-806. r, Pearson correlation coefficient.

FIG. 3A is a picture that shows the stability of the non-covalent association of gp120 with Env complexes, the detergent-solubilized, His6-tagged Envs were captured on Ni-NTA beads and Western blotted with rabbit anti-gp120 antibody or the 4E10 anti-gp41 antibody. FIG. 3B is a Western blot of VLPs prepared from the supernatants of A549-Gag/Env cells expressing Gag-mCherry and HIV-$1_{AD8}$ Env. Triton X-100 lysates of VLPs were incubated with DMSO or the indicated molecules. Env was then captured on Ni-NTA beads and Western blotted as described in FIG. 3A. FIG. 3C is a Western blot of Triton X-00 lysates of A549 or HOS cells expressing Envs from different HIV-1 strains were incubated with Ni-NTA beads in the presence of the indicated molecules, and then the captured molecules were Western blotted as described in FIG. 3A. FIG. 3D is a Western blot of HOS cells transiently expressing the indicated HIV-$1_{AD8}$ Env variants were lysed, as described above. The cell lysates were incubated with DMSO, BMS-806 or sCD4 prior to precipitation with Ni-NTA beads and Western blotting, as described in FIG. 3A. The experiments in FIGS. 3B-3D were performed at least twice, and a representative experiment is shown.

FIG. 10A is a Western blot of monomeric soluble HIV-$1_{AD8}$ gp120 precipitated by the indicated antibodies in the absence or presence of 10 μM BMS-806. The precipitated proteins were Western blotted with a rabbit anti-gp120 antiserum. FIG. 10B is a Western blot of A549 cells expressing HIV-$1_{AD8}$ Env incubated with the indicated antibodies in the absence or presence of BMS-806. The cells were then washed and lysed, and the cell lysates were incubated with Protein A-Sepharose beads. No BMS-806 was added to the cell lysates in this case. Precipitates were analyzed by Western blotting with a rabbit anti-gp120 antibody (upper panels) or the 4E10 anti-gp41 antibody (lower panels).

FIG. 12A is a picture rendering the best docked pose of AEG-II-168 (pink sticks) with the crystallographic pose of BMS-529 (yellow sticks) superimposed. FIG. 12B is a residue interaction map of AEG-II-168.

FIG. 13A is a Western blot of the recognition of cell-surface HIV-$1_{AD8}$ Env by the indicated antibodies in the absence or presence of BMS-806 was assessed as described in the FIG. 1A legend. FIGS. 13B and 13C are Western blots of the recognition of HIV-$1_{AD8}$ Env on the surface of VLPs by the indicated antibodies in the absence or presence of BMS-806 was assessed as described in the FIG. 2C legend. The heavy chain (HC) of the antibody is shown in FIG. 13C.

DETAILED DESCRIPTION OF ILLUSTRATIVE EMBODIMENTS

Figure 1A:
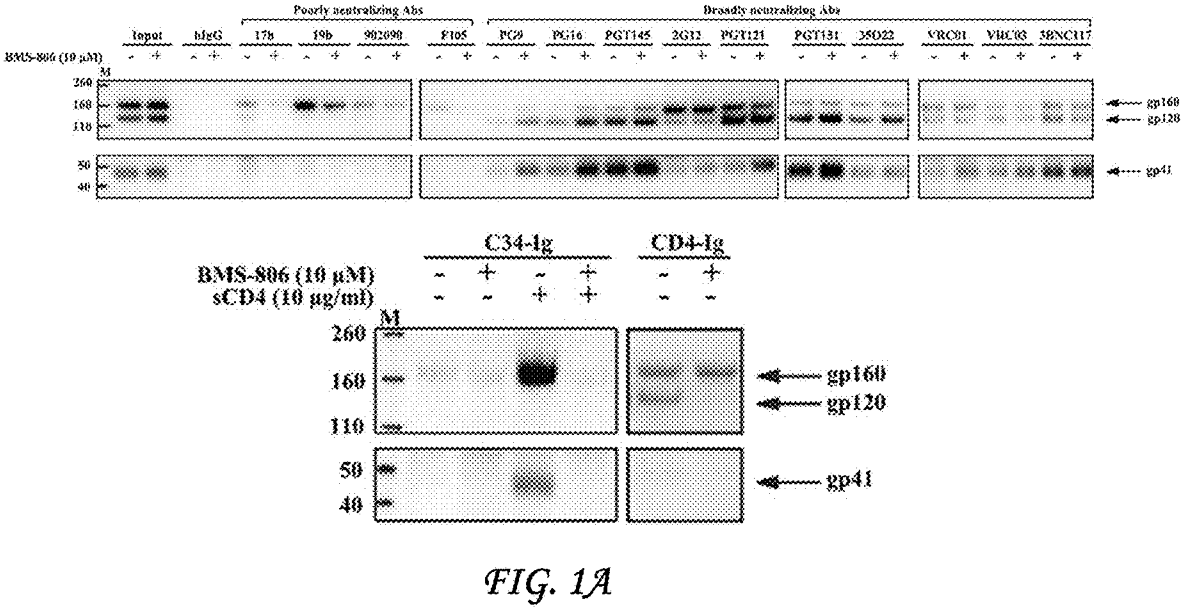
FIGS. 1A-1C show the effect of BMS-806 on the conformation of cell-surface Env.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The term "alkyl," when used alone or as part of a substituent group, refers to a straight- or branched-chain alkyl group having from 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples. An alkyl moiety is optionally substituted with one, two, or three substituents selected from halo (F, Cl, Br, or I, preferably F), —$C_{1-6}$haloalkyl, —OH, —$C_{1-6}$alkoxy, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "$C_{1-6}$alk" refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond.

The terms "haloalkyl" and "halogenated alkyl" are interchangeable and, when used alone or as part of a substituent group, refer to an alkyl group as described above having one, two, or three halogen atoms attached to a single carbon atom. Preferably, the halogen is F. In some embodiments, haloalkyl includes perfluoroalkyl groups whereby the alkyl group is terminated with a $CF_3$, $CH_2F$, or $CHF_2$. Examples of haloalkyl groups include $CF_3$, $CHF_2$, $CH_2F$, $CH_2CF_3$, $CHFCF_3$, $CF_2CF_3$, $CH_2CHF_2$, $CH_2CH_2F$, $CHFCH_3$, $CF_2CH_3$, $CHFCHF_2$, $CF_2CHF_2$, among others, and groups that in light of the ordinary skill in the art and the teachings provided herein would be considered equivalent to any one of the foregoing examples. A haloalkyl moiety is optionally substituted with one, two, or three substituents selected from —OH, —$C_{1-6}$alkoxy, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "alkoxy," when used alone or as part of a substituent group, refers to a straight- or branched-chain alkoxy group, i.e., O-alkyl, having from 1 to 6 carbons atoms ("$C_{1-6}$"), in the chain. Examples of alkoxy groups include methoxy (OMe, $C_1$alkoxy) ethoxy (OEt, $C_2$alkoxy), n-propoxy (OnPr, $C_3$alkoxy), isopropoxy (OiPr, $C_3$alkoxy), butoxy (OBu, $C_4$alkoxy), isobutoxy (OiBu, $C_4$alkoxy), sec-butoxy (OsBu, $C_4$alkoxy), tert-butoxy (OtBu, $C_4$alkoxy), pentoxy ($C_5$alkoxy), isopentoxy ($C_5$alkoxy), tert-pentoxy ($C_5$alkoxy), hexoxy ($C_6$alkoxy), isohexoxy ($C_6$alkoxy), and groups that in light of the ordinary skill in the art and the teachings provided herein would be considered equivalent to any one of the foregoing examples. An alkoxy moiety is optionally substituted with one, two, or three substituents selected from halo (F, Cl, Br, or I, preferably F), —$C_{1-6}$ haloalkyl, —OH, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "optionally substituted" as used herein refers to the particular group having one or more substituents selected from halo (F, Cl, Br, or I, preferably F), —OH, —$C_{1-6}$ alkoxy, —$C_{1-6}$haloalkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "diazirinyl" as used herein refers to the following group. The diazirinyl group is optionally substituted with one halo (F, Cl, Br, or I, preferably F), —OH, —$C_{1-6}$alkoxy, —$C_{1-6}$haloalkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

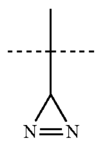

"Heterocyclyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18: refers to each integer in the given range, e.g., "3 to 18 ring atoms" means that the heterocyclyl group may consist of 3 ring atoms, 4 ring atoms, etc., up to and including 18 ring atoms. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of heterocyclyl radicals include, but are not limited to, azepanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. "Heterocyclyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic. A heterocyclyl moiety is optionally substituted with one, two, or three substituents selected from halo (F, Cl, Br, or I, preferably F), —$C_{1-6}$alkyl, —$C_{1-6}$alkoxy, —$C_{1-6}$haloalkyl, —OH, —CN, —$NH_2$, —NH($C_{1-6}$alkyl), —NH($C_{1-6}$ alkyl)$_2$, $C_{3-8}$cycloalkyl, heterocyclyl, aryl, or heteroaryl.

The term "cycloalkyl" refers to monocyclic, non-aromatic hydrocarbon groups having from 3 to 10 carbon atoms ("$C_{3-10}$"), preferably from 3 to 6 carbon atoms ("$C_3$-6"). Examples of cycloalkyl groups include, for example, cyclopropyl ($C_3$), cyclobutyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like. A cycloalkyl is optionally substituted with one, two, or three substituents selected from halo (F, Cl, Br, or I, preferably F), —OH, —$C_{1-6}$alkyl, —$C_{1-6}$alkoxy, —$C_{1-6}$haloalkyl, —CN, —$NH_2$, —NH($C_{1-6}$ alkyl), —NH($C_{1-6}$alkyl)$_2$, $C_{3-8}$cycloalkyl, heterocyclyl, aryl, or heteroaryl.

The term "aryl" refers to carbocyclic aromatic groups having from 6 to 10 carbon atoms ('$C_{6-10}$") such as phenyl, naphthyl, and the like. An aryl is optionally substituted with one, two, or three substituents selected from halo (F, Cl, Br, or I, preferably F), —OH, —$C_{1-6}$alkyl, —$C_{1-6}$alkoxy, —$C_{1-6}$ haloalkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl. In some embodiments, the aryl is substituted with one halo. In other embodiments, the aryl is substituted with one F. In still other embodiments, the aryl is phenyl and is optionally substituted with one halo. In yet further embodiments, the aryl is phenyl and is optionally substituted with one F.

"Heteroaryl" refers to a 5- to 18-membered aromatic radical, e.g., $C_{5-18}$heteroaryl, that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range, e.g., "5 to 18 ring atoms" means that the heteroaryl group may contain 5 ring atoms, 6 ring atoms, etc., up to and including 18 ring atoms. An N-containing heteroaryl moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). A heteroaryl is optionally substituted with one, two, or three substituents selected from halo (F, Cl, Br, or I, preferably F), $C_{1-6}$alkyl, $C_{1-6}$alkoxy, $C_{1-6}$haloalkyl, —OH, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The terms "halogen" and "halo" represent chlorine, fluorine, bromine, or iodine. The term "halo" represents chloro, fluoro, bromo, or iodo. In some embodiments, halo is chloro. In other embodiments, halo is fluoro. In further embodiments, halo is bromo. In still other embodiments, halo is iodo.

"Compounds of the disclosure," and equivalent expressions, are meant to embrace compounds of the Formula (I) as described herein, which expression includes the pharmaceutically acceptable salts, where the context so permits. Similarly, reference to intermediates, whether or not they themselves are claimed, is meant to embrace their salts, and solvates, where the context so permits. Similarly, the term "compound(s) of formula (I)" includes those compounds of "formula (I)," as well as compounds of any of the formula (I) subgenera.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The present disclosure provides novel compounds that useful for treating HIV. The compounds are long-acting, stabilizing a State-1-like conformation of membrane Env for at least 21 days. Thus, the present disclosure provides compounds of Formula (I) or a pharmaceutically acceptable salt thereof.

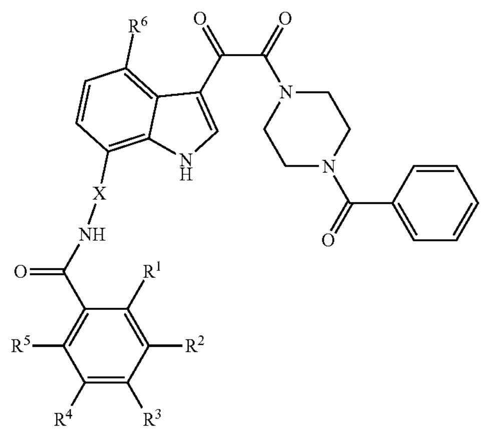

(I)

In these compounds, $R^1$ to $R^5$ are, independently, H, halo, optionally substituted $C_{1-6}$alkyl, optionally substituted diazirinyl, or $N_3$; preferably the halo is F, Cl, or Br, and more preferably F. In other embodiments, $R^1$ to $R^5$ are, independently, H, halo, optionally substituted diazirinyl, or $N_3$; preferably the halo is F, Cl, or Br, and more preferably F. In further embodiments, $R^1$ to $R^5$ are, independently, H or halo; preferably the halo is F, Cl, or Br, and more preferably F. In yet other embodiments, $R^1$ to $R^5$ are, independently, halo or $N_3$; preferably the halo is F, Cl, or Br, and more preferably F. In still further embodiments, $R^1$ to $R^5$ are, independently, halo or diazirinyl; preferably the halo is F, $C_1$, or Br, and more preferably F. In other embodiments, $R^1$ to $R^5$ are H. In further embodiments, $R^1$ to $R^5$ are halo, preferably F, Cl, or Br, and more preferably F. In still other embodiments, four of $R^1$ to $R^5$ are halo and one of $R^1$ to $R^5$ is $N_3$; preferably the halo is F, Cl, or Br, and more preferably F. In yet other embodiments, $R^1$, $R^2$, $R^4$, and $R^5$ are halo and $R^3$ is $N_3$; preferably the halo is F, Cl, or Br, and more preferably F. In still further embodiments, one of $R^1$ to $R^5$ are optionally substituted diazirinyl. In other embodiments, the diazirinyl is optionally substituted with halo, $C_{1-6}$alkyl, or $C_{1-6}$haloalkyl. In some aspects, the diazirinyl is optionally substituted with $C_{1-6}$haloalkyl such as trifluoromethyl. In further aspects, the diazirinyl is optionally substituted with halo. In other aspects, the diazirinyl is optionally substituted with $C_{1-6}$alkyl. In still further aspects, the diazirinyl is

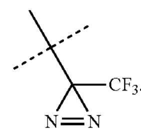

In the compounds of formula (I), $R^6$ is H, $C_{1-6}$alkyl, or $C_{1-6}$alkoxy. In some embodiments, $R^6$ is H. In other embodiments, $R^6$ is $C_{1-6}$alkoxy. In further embodiments, $R^6$ is methoxy, ethoxy, propoxy, butoxy, pentoxy, or hexoxy. In yet other embodiments, $R^6$ is methoxy. In still further embodiments, $R^6$ is $C_{1-6}$alkyl. In other embodiments, $R^6$ is methyl, ethyl, propyl, butyl, pentyl, or hexyl. In further embodiments, $R^6$ is methyl.

X in the compounds of formula (I) is absent, -furanyl-, or furanyl-$C_{1-6}$alk-. In some embodiments, X is absent. In other embodiments, X is furanyl. In further embodiments, X is 2,3-furanyl, 2,4-furanyl, 2,5-furanyl, 3,4-furanyl, 3,5-furanyl, or 4,5-furanyl. In still other embodiments, X is 2,5-furanyl. In yet further embodiments, X is furanyl-$C_{1-6}$alk-. In other embodiments, X is -2-furanyl-3-$C_{1-6}$alk-, -2-furanyl-4-$C_{1-6}$alk-, -2-furanyl-5-$C_{1-6}$alk-, -3-furanyl-4-$C_{1-6}$alk-, -3-furanyl-5-$C_{1-6}$alk-, or -4-furanyl-5-$C_{1-6}$alk-. In further embodiments, X is -2-furanyl-5-$C_{1-6}$alk-. In yet other embodiments, X is furanyl-$CH_2$—. In still further embodiments, X is -2-furanyl-3-$CH_2$—, -2-furanyl-4-$CH_2$—, -2-furanyl-5-$CH_2$—, -3-furanyl-4-$CH_2$, -3-furanyl-5-$CH_2$—, or -4-furanyl-5-$CH_2$—. In still other embodiments, X is -2-furanyl-5-$CH_2$—.

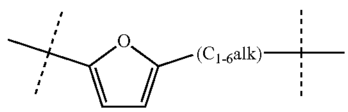

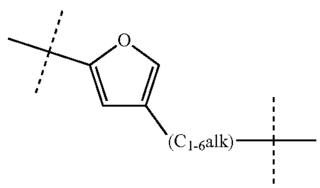

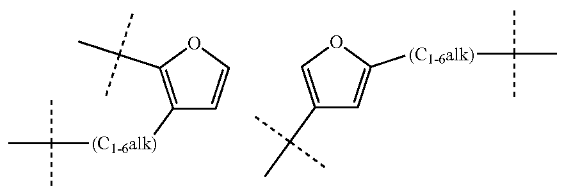

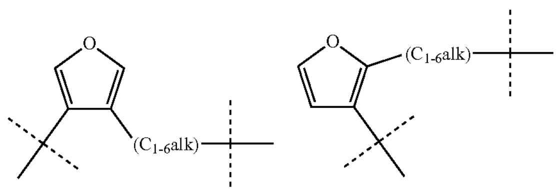

In some aspects, the present disclosure provides compounds of formula (IA) or pharmaceutically acceptable salts thereof, wherein $R^1$-$R^6$ are defined herein:

(IA)

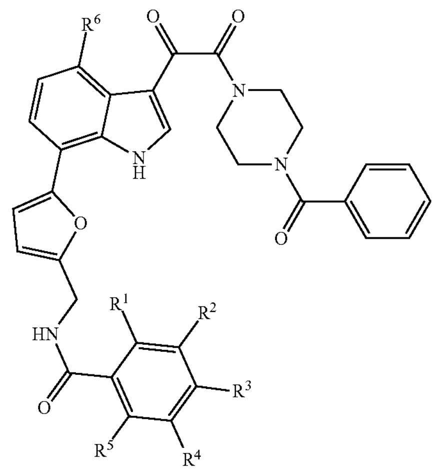

In other aspects, the present disclosure provides compounds of formula (IB) or pharmaceutically acceptable salts thereof, wherein $R^1$-$R^6$ are defined herein:

(IB)

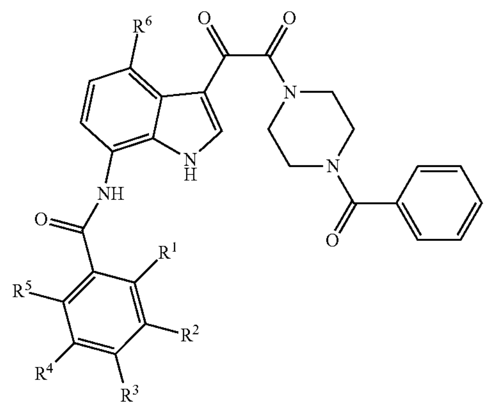

In further aspects, the present disclosure provides compound AEG-II-159 or pharmaceutically acceptable salts thereof:

AEG-II-159

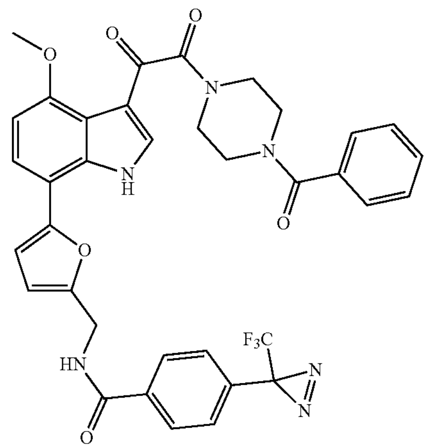

In further aspects, the present disclosure provides compound AEG-II-168 or pharmaceutically acceptable salts thereof:

AEG-II-168

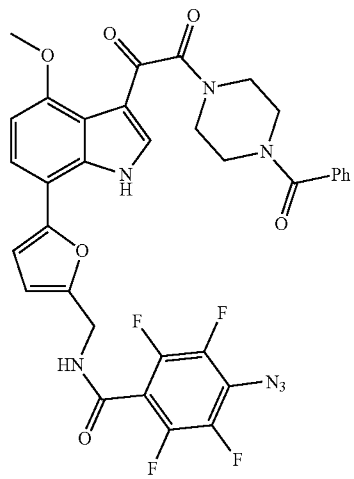

In further aspects, the present disclosure provides compound AEG-III-032 or pharmaceutically acceptable salts thereof:

AEG-III-032

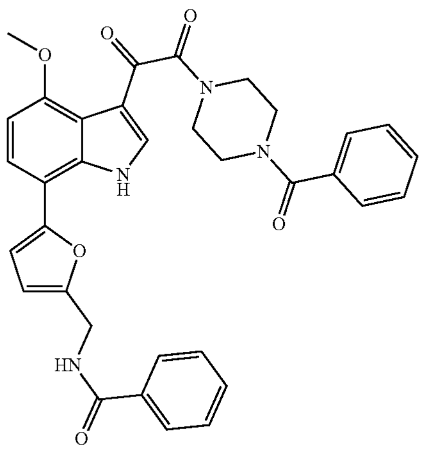

In further aspects, the present disclosure provides compound AEG-III-087 or pharmaceutically acceptable salts thereof:

AEG-III-087

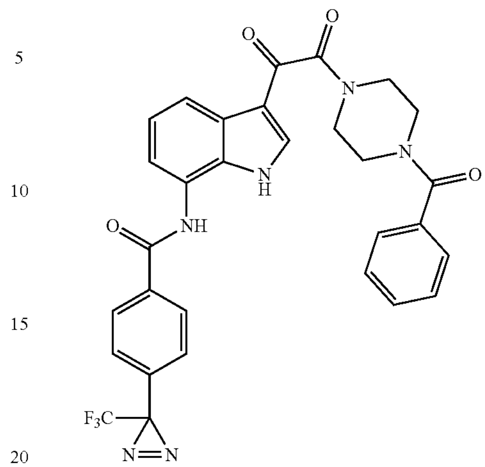

In further aspects, the present disclosure provides compound AEG-III-095 or pharmaceutically acceptable salts thereof.

AEG-III-095

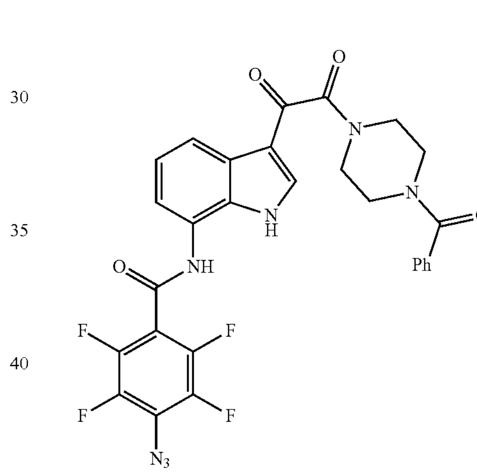

In further aspects, the present disclosure provides compound AEG-III-096 or pharmaceutically acceptable salts thereof.

AEG-III-096

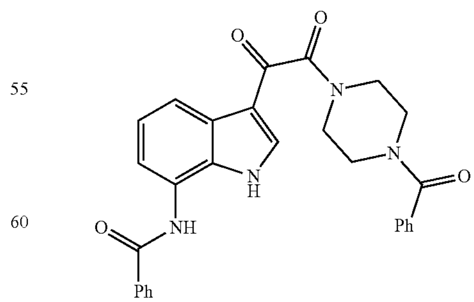

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In some embodiments, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids.

In other embodiments, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyl dimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1 n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like.

The disclosure also provides pharmaceutical compositions that contain one or more compounds discussed herein, optionally containing a pharmaceutically acceptable excipient. In some embodiments, a compound described above is present in a single composition. In other embodiments, a compound described above is combined with one or more excipients as described below.

The pharmaceutical compositions include a compound described herein formulated neat or with one or more pharmaceutically acceptable excipients for administration, the proportion of which is determined by the solubility and chemical nature of the compound, chosen route of administration and standard pharmacological practice. The pharmaceutically acceptable excipient may be solid or liquid.

The compound or composition may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epidurally, among others.

Although the compound may be administered alone, it may also be administered in the presence of one or more pharmaceutically acceptable excipient that are physiologically compatible. In some embodiments, the pharmaceutically acceptable excipient is a carrier.

The carrier may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In some embodiments, the compound is dissolved a liquid carrier. In some embodiments, the compound is suspended in a liquid carrier. One of skill in the art of formulations would be able to select a suitable liquid carrier, depending on the route of administration. In other embodiments, the liquid carrier includes, without limitation, water, organic solvents, oils, fats, or mixtures thereof. In yet other embodiments, the liquid carrier is water containing cellulose derivatives such as sodium carboxymethyl cellulose. In further embodiments, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the compound may be formulated in a solid carrier. In some embodiments, the composition may be compacted into a unit dose form, i.e., tablet or caplet. In other embodiments, the composition may be added to unit dose form, i.e., a capsule. In further embodiments, the composition may be formulated for administration as a powder. The solid carrier may perform a variety of functions, i.e., may perform the functions of two or more of the pharmaceutically acceptable excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable pharmaceutically acceptable excipients, including those described below.

Examples of pharmaceutically acceptable excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5th Edition, Eds.: Rowe, Sheskey, and Owen, APhA Publications (Washington, DC), Dec. 14, 2005, which is incorporated herein by reference.

The pharmaceutical composition described herein may be prepared by those skilled in the art. In some embodiments, the pharmaceutical compositions are prepared by combining a compound described herein with a pharmaceutically acceptable excipient.

As discussed above, the compounds described herein are useful in methods related to HIV. Thus, in some embodiments, the present disclosure provides methods for treating human immunodeficiency virus in a subject in need thereof by administering to a compound described herein to the subject in need thereof. The disclosure also provides for administering a pharmaceutical composition containing one or more compounds of the disclosure.

The term "subject" as used herein refers to a mammalian animal. In some embodiments, the subject is a human. In other embodiments, the subject is a veterinary or farm animal, a domestic animal or pet, or animal normally used for clinical research.

"Treating" any disease or disorder refers, in some embodiments, to ameliorating the disease or disorder (i.e., arresting or reducing the development of the disease or at least one of the clinical symptoms thereof). In some embodiments, "treating" or "treatment" refers to ameliorating at least one physical parameter, which may not be discernible by the subject. In other embodiments, "treating" or "treatment" refers to modulating the disease or disorder, either physically, (e.g., stabilization of a discernible symptom), physiologically, (e.g., stabilization of a physical parameter), or both. In further embodiments, "treating" or "treatment" refers to delaying the onset of the disease or disorder.

As used herein, "HIV" refers to any virus that can infect a host cell of a subject through activation of the gp120 envelope glycoproteins (Env gps). "HIV" encompasses all strains of HIV-1 and HIV-2. The compounds described herein, however, are also useful to treat other immunodeficiency viruses expressing gp120 such as some strains of simian immunodeficiency virus SIV. In some embodiments, HIV refers to HIV-1. In other embodiments, HIV refers to HIV-2.

As used herein "gp120" refers to the gp120 envelope glycoprotein, and "Env gps" refers to the complete envelope glycoprotein complex which is a trimer of three gp120s and three gp41s.

In other embodiments, the disclosure provides methods of inhibiting transmission of HIV to a cell. These methods comprise contacting the HIV with a therapeutically effective amount of one or more of the compounds described herein.

In further embodiments, the disclosure provides methods of inhibiting the progression of HIV infection in a cell. Such methods comprise contacting HIV with a therapeutically effective amount of one or more of the compounds described herein.

In yet other embodiments, methods of neutralizing HIV are provided and these methods include contacting HIV with a therapeutically effective amount of one or more of the compounds described herein.

In still further embodiments, methods of neutralizing HIV-1 and provided. These methods comprise (i) contacting HIV-1 with a therapeutically effective amount of one or more compounds described herein, thereby forming HIV-1 having gp120 in a specific conformational state; and (ii) contacting the HIV-1 with an antibody.

In certain embodiments, methods of treating or preventing HIV infection are provided. These methods comprise (i) administering to a subject in need thereof, a therapeutically effective amount of an antibody; and (ii) co-administering to the subject a therapeutically effective amount of a compound described herein.

In certain aspects, the antibody is a monoclonal antibody. In further aspects, the antibody is a monoclonal antibody directed against CD4-induced (CD4i) epitopes or the V3 region. In other aspects, the antibody is an anti-gp120 antibody.

In some embodiments, a therapeutically effective amount of a compound described herein is administered to a subject. A "therapeutically effective amount" means an amount or dose sufficient to generally bring about the desired therapeutic benefit in subjects in need of such treatment for the designated disease, disorder, or condition. Therapeutically effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

These therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In some embodiments, the therapeutically effective amount for the first dose is higher than the therapeutically effective amount for one or more of the subsequent doses. In other embodiments, the therapeutically effective amount for the first dose is lower than the therapeutically effective amount for one or more of the subsequent doses.

Also provided herein are kits or packages containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, prefilled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In some embodiments, the package has indicators for each period. In other embodiments, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Aspects

Aspect 1. A compound of Formula (I):

(I)

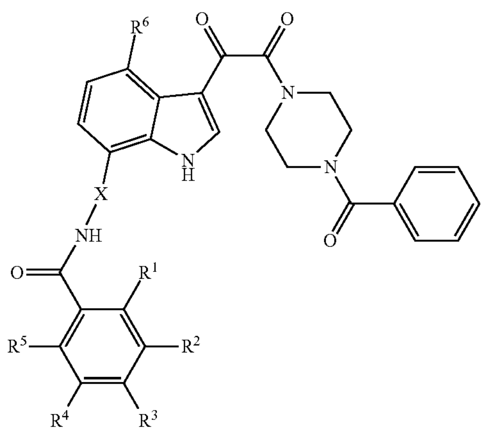

wherein:

$R^1$ to $R^5$ are, independently, H, halo, optionally substituted $C_{1-6}$alkyl, optionally substituted diazirinyl, or $N_3$;

$R^6$ is H, $C_{1-6}$alkyl, or $C_{1-6}$alkoxy; and

X is absent, -furanyl-, or furanyl-$C_{1-6}$alk-;

or a pharmaceutically acceptable salt thereof.

Aspect 2. The compound of Aspects 1, that is a compound of formula (IA):

(IA)

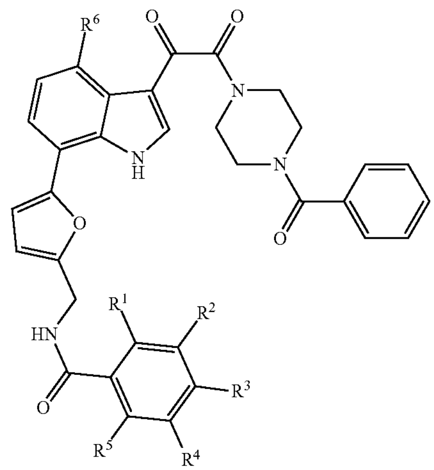

or a pharmaceutically acceptable salt thereof.

Aspect 3. The compound of Aspect 1, that is of formula (IB):

(IB)

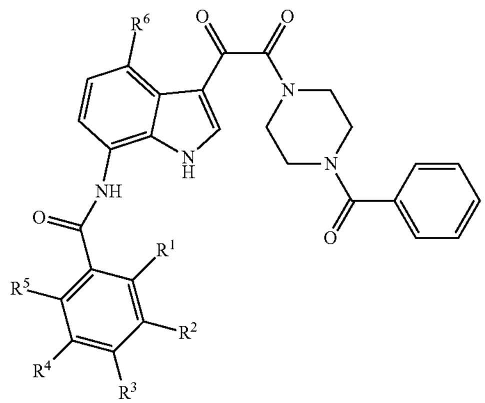

or a pharmaceutically acceptable salt thereof.

Aspect 4. The compound of any one of the preceding Aspects, wherein $R^1$ to $R^5$ are, independently, H, halo, optionally substituted diazirinyl, or $N_3$.

Aspect 5. The compound of any one of Aspects 1-4, wherein $R^1$ to $R^5$ are halo.

Aspect 6. The compound of any one of Aspects 1-4, wherein four of $R^1$ to $R^5$ are halo and one of $R^1$ to $R^5$ is $N_3$.

Aspect 7. The compound of any one of Aspects 1-4, wherein $R^1$, $R^2$, $R^4$, and $R^5$ are halo and $R^3$ is $N_3$.

Aspect 8. The compound of any one of the preceding Aspects, wherein the halo is F, Cl, or Br, preferably F.

Aspect 9. The compound of any one of the preceding Aspects, wherein $R^1$ to $R^5$ are H.

Aspect 10. The compound of any one of Aspects 1-4, wherein one of $R^1$ to $R^5$ are optionally substituted diazirinyl.

Aspect 11. The compound of any one of Aspects 1-4 or 10, wherein the diazirinyl is optionally substituted with halo, $C_{1-6}$alkyl, or $C_{1-6}$haloalkyl.

Aspect 12. The compound of any one of Aspects 1-4, 10, or 11, wherein the diazirinyl is optionally substituted with $C_{1-6}$haloalkyl such as trifluoromethyl.

Aspect 13. The compound of any one of Aspects 1-4 or 10-12, wherein the diazirinyl is

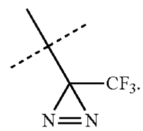

Aspect 14. The compound of any one of the preceding Aspects, wherein $R^6$ is H.

Aspect 15. The compound of any one of Aspects 1-13, wherein $R^6$ is $C_{1-6}$alkoxy such as methoxy, ethoxy, propoxy, butoxy, pentoxy, or hexoxy, preferably methoxy.

Aspect 16. The compound of any one of Aspects 1-13, wherein $R^6$ is $C_{1-6}$alkyl, such as methyl, ethyl, propyl, butyl, pentyl, or hexyl.

Aspect 17. The compound of any one of Aspects 1 or 3-16, wherein X is absent.

Aspect 18. The compound of any one of Aspects 1, 2, or 4-16, wherein X is furanyl, such as 2,3-furanyl, 2,4-furanyl, 2,5-furanyl, 3,4-furanyl, 3,5-furanyl, or 4,5-furanyl, preferably 2,5-furanyl.

Aspect 19. The compound of any one of Aspects 1, 2 or 4-16, wherein X is furanyl-$C_{1-6}$alk- such as -2-furanyl-3-$C_{1-6}$alk-, -2-furanyl-4-$C_{1-6}$alk-, -2-furanyl-5-$C_{1-6}$alk-, -3-furanyl-4-$C_{1-6}$alk-, -3-furanyl-5-$C_{1-6}$alk-, or -4-furanyl-5-$C_{1-6}$alk-, preferably -2-furanyl-5-$C_{1-6}$alk-, preferably furanyl-$CH_2$— such as -2-furanyl-3-$CH_2$—, -2-furanyl-4-$CH_2$—, -2-furanyl-5-$CH_2$—, -3-furanyl-4-$CH_2$, -3-furanyl-5-$CH_2$—, or -4-furanyl-5-$CH_2$—, or more preferably -2-furanyl-5-$CH_2$—.

Aspect 10. The compound of Aspect 1, that is:

AEG-II-159

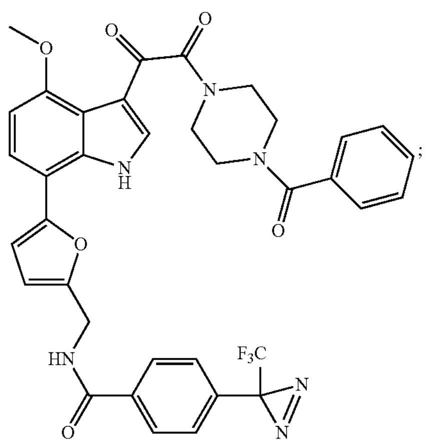

-continued

AEG-II-168

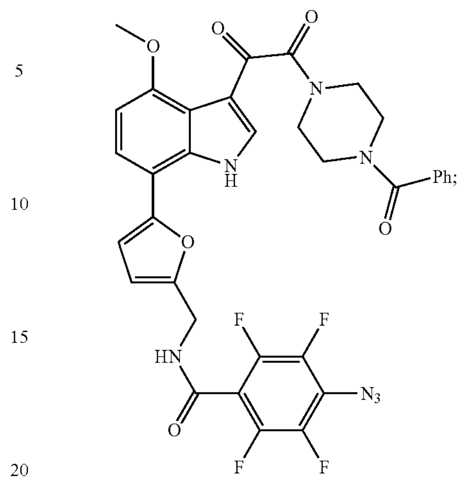

AEG-III-032

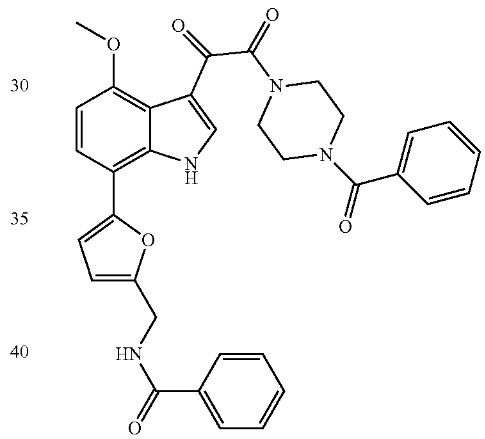

AEG-III-087

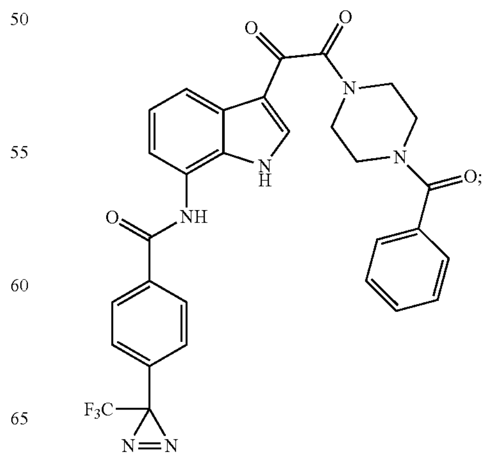

-continued

AEG-III-095

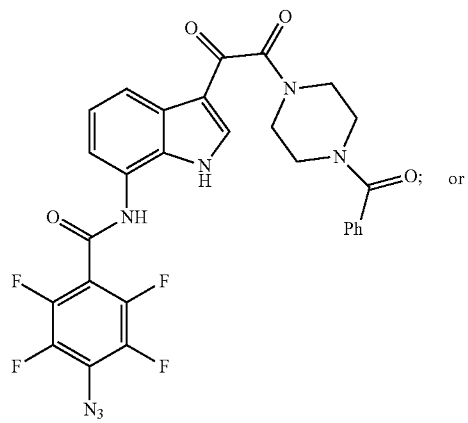

or

AEG-III-096

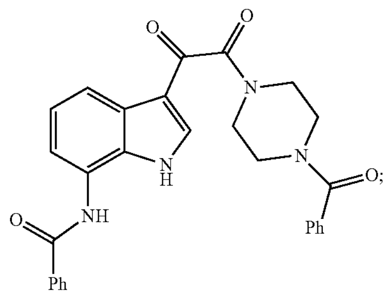

or a pharmaceutically acceptable salt thereof.

Aspect 21. A pharmaceutical composition comprising one or more compounds of any one of the preceding Aspects.

Aspect 22. A method for treating human immunodeficiency virus (HIV) in a subject in need thereof, comprising administering one or more compounds of any one of Aspects 1-20 or pharmaceutical composition of Aspect 21 to the subject in need thereof.

Aspect 23. The method of Aspect 22, wherein the HIV is HIV-1.

Aspect 24. A method for stabilizing the state-1 conformation of the HIV-1 envelope glycoproteins, comprising administering one or more compounds of any one of Aspects 1-20 or pharmaceutical composition of Aspect 21 to the subject in need thereof.

EXAMPLES

BMS-378806 (BMS-806) and BMS-626529 (Temsavir; BMS-529) were purchased from Selleckchem and APExBIO, respectively.

All reagents were purchased from commercially available sources and used as received. Reactions were magnetically stirred under a nitrogen atmosphere, unless otherwise noted and reactions were monitored by either thin layer chromatography (TLC) with 0.25 mm E. Merck pre-coated silica gel plates or liquid chromatography mass spectrometry (LCMS). Proton ($^1H$) and carbon ($^{13}C$) NMR spectra were recorded on a Bruker Avance III 500-MHz spectrometer or on a Bruker DRX500 500-MHz spectrometer. Chemical shifts (δ) are reported in parts per million (ppm) relative to chloroform (δ 7.26) for $^1H$ NMR, and (δ 77.0) for $^{13}C$ NMR. Infrared spectra were recorded using a JASCO 480-Plus FT-IR spectrometer, or a Perkin-Elmer Spectrum Two FT-IR spectrometer. Accurate mass measurement data were acquired on Waters Instruments. Waters software calibrates and reports by use of neutral atomic masses. The mass of the electron is not included. Preparative scale HPLC was preformed with a Gilson 333/334 preparative pump system equipped with a 5 mL injection loop, Sunfire C18 OBD column (5 μm packing material, 19×100 mm column dimensions) equipped with a UV-Vis dual wavelength (210 and 254 nm) detector and 215 liquid handling module. Solvent systems were comprised of $H_2O$ containing 0.1% trifluoroacetic acid, and acetonitrile containing 0.1% trifluoroacetic acid. Lyophilization was performed in a Labconco FreeZone 12 Plus lyophilizer (0.035 mbar). The purity of new compounds was judged by NMR.

Example 1: Synthesis of AEG-II-159

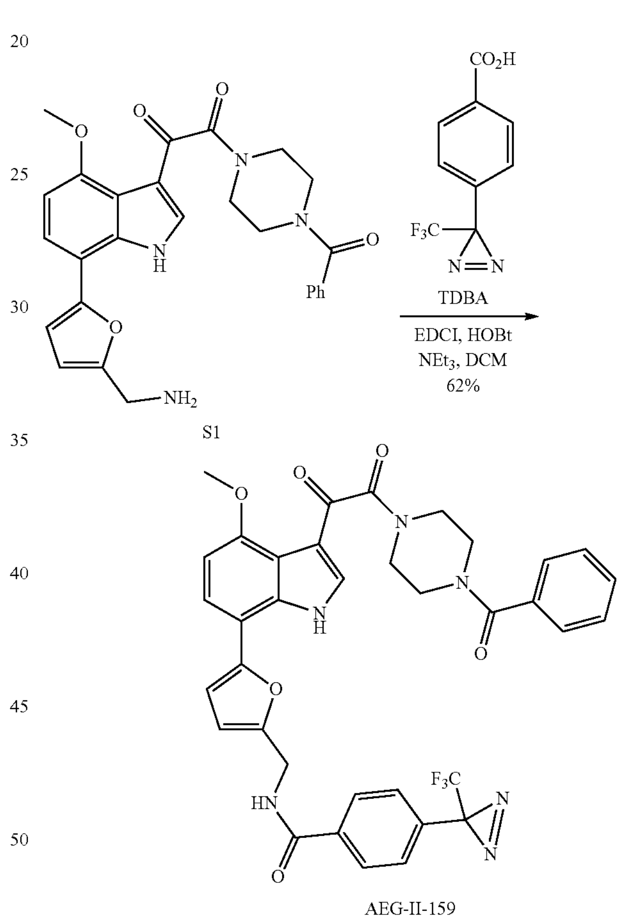

S1

AEG-II-159

To a solution of S1 (0.074 g, 0.15 mmol) (Parker, Chem Sci 5, 2311-2317, 2014), TDBA (0.052 g, 0.23 mmol, 1.5 eq.), EDCI.HCl (0.071 g, 0.46 mmol, 3 eq.), and HOBt·$H_2O$ (0.070 g, 0.46 mmol, 3 eq.) in $CH_2Cl_2$ (6.8 mL) in a round bottom flask shielded from light under $N_2$ was added $NEt_3$ (0.11 mL, 0.76 mmol, 5 eq.). After 90 min, no starting material was observed by TLC. The crude reaction mixture was purified by flash column chromatography ($SiO_2$, 50-100% EtOAc/Hexanes) to afford AEG-II-159 as a (0.066 g, 62%) yellow solid.

$^1H$ NMR (500 MHz, $CDCl_3$) δ 11.26 (s, 1H), 8.15 (d, 1H, J=3.3 Hz), 7.82 (app. d, 1H, J=6.6 Hz), 7.42 (br. s, 5H), 7.38 (d, 1H, J=8.3 Hz), 7.20 (d, 2H, J=8.2 Hz), 7.07 (t, 1H, J=6.2

Hz), 6.66 (d, 1H, J=8.3 Hz), 6.52 (d, 1H, J=3.3 Hz), 6.33 (d, 1H, J=3.3 Hz), 4.66 (d, 2H, J=6.1 Hz), 3.91 (s, 3H), 3.97-3.38 (m, 8H). $^{13}C$ NMR (500 MHz, $CDCl_3$): 170.9, 167.9, 167.8, 153.8, 152.9, 149.6, 135.7, 135.2, 134.9, 134.4, 133.0, 130.3, 128.8, 127.7, 127.2, 126.8, 120.9, 120.3, 115.6, 115.1, 109.5, 109.4, 103.9, 77.4, 56.1, 37.4, 29.9, 28.6, 28.3. IR $\nu_{max}$ 3849, 3404, 2917, 2849, 2359, 1629, 1577, 1541, 1511, 1467, 1432, 1284, 1155. HRMS (ESI) m/z 699.2180 [calcd for $(M+H)^+$ 699.2179]

Example 2: Synthesis of AEG-II-168

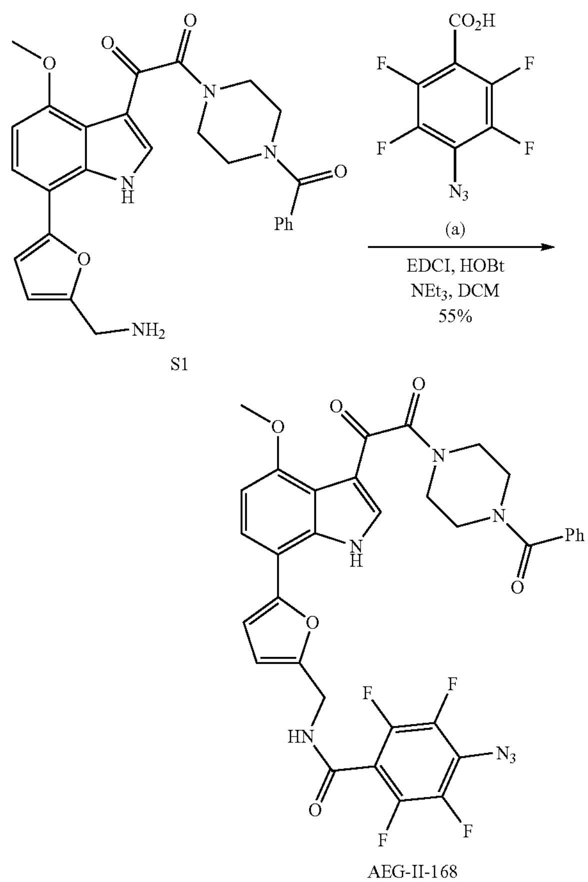

S1

AEG-II-168

To a solution of S1 (0.100 g, 0.206 mmol), (a) (0.073 g, 0.31 mmol, 1.5 eq.), EDCI·HCl (0.096 g, 0.62 mmol, 3 eq.), and HOBt·$H_2O$ (0.095 g, 0.62 mmol, 3 eq.) in $CH_2Cl2$ (6.8 mL) in a round bottom flask shielded from light under $N_2$ was added $NEt_3$ (0.14 mL, 1.03 mmol, 5 eq.). The reaction was allowed to proceed overnight. The crude reaction mixture was concentrated, and purified by flash column chromatography ($SiO_2$, 60-100% EtOAc/Hexanes) to afford AEG-II-168 (0.080 g, 55%) as a viscous orange oil.

$^1H$ NMR (500 MHz, $CDCl_3$) δ 10.95 (s, 1H), 8.06 (app. s, 1H), 7.43 (m, 5H), 7.20 (m, 1H), 6.68 (d, 1H, J=8.3 Hz), 6.56 (d, 1H, J=3.3 Hz), 6.37 (d, 1H, J=3.3 Hz), 4.68 (d, 2H, J=6.1 Hz), 3.90 (s, 3H), 3.97-3.30 (m, 8H). $^{13}C$ NMR (500 MHz, $CDCl_3$): 185.8, 170.8, 167.6, 159.3, 153.7, 152.9, 148.9, 145.3, 139.4, 139.3, 136.1, 134.9, 139.3, 136.1, 134.9, 134.2, 130.2, 128.7, 127.1, 122.3, 120.5, 115.3, 114.8, 110.6, 110.4, 110.3, 109.7, 109.2, 109.1, 108.9, 104.1, 103.9, 55.9, 41.6, 37.3, 29.7. IR $\nabla_{max}$ 3299, 2918, 2849, 2360, 2341, 2128, 1631, 1545, 1510, 1486, 1429, 1401, 1364, 1271, 1131. HRMS (ESI) m/z 704.1859 [calcd for $C_{34}H_{25}F_4N_7O_6$ $(M+H)^+$ 704.1881]

Example 3: Synthesis of AEG-III-032

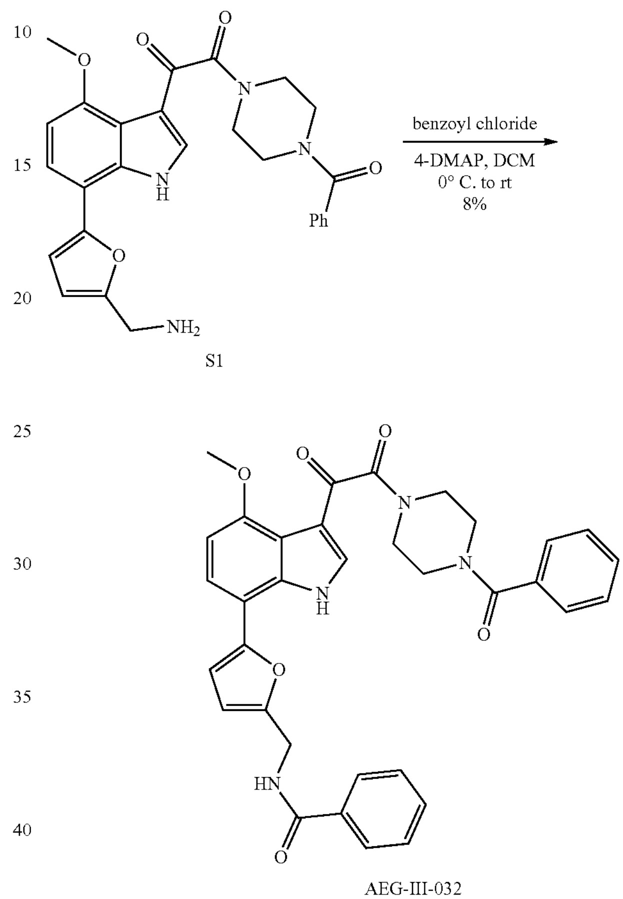

S1

AEG-III-032

To a solution of S1 (0.039 g, 0.081 mmol) in $CH_2Cl_2$ (2 mL) under $N_2$ at 0° C. was added 4-DMAP (0.020 g, 0.16 mmol, 2 eq.). After 10 min, benzoyl chloride was added (0.023 g, 0.16 mmol, 2 eq.) and the reaction was allowed to gradually warm to room temperature overnight. The crude reaction mixture was concentrated and subjected to flash column chromatography ($SiO_2$, 50% EtOAc/Hexanes—20% MeOH/EtOAc), concentrated, dissolved in 1.5 mL ACN+0.8 mL water, and further purified by reverse phase HPLC (15 mL/min 45-80% ACN/$H_2O$+0.1% TFA, 6 min) to afford AEG-III-032 (0.004 g, 8%).

$^1H$ NMR (500 MHz, $CDCl_3$) δ 11.31 (s, 1H), 8.21 (s, 1H), 7.80 (d, 1H, J=7.3 Hz), 7.52 (t, 1H, J=7.5 Hz), 7.43 (m, 8H), 6.99 (t, 1H, J=6.4 Hz), 6.69 (d, 1H, J=8.3 Hz), 6.53 (d, 1H, J=3.3 Hz), 6.34 (d, 1H, J=3.3 Hz), 4.69 (d, 1H, J=6.1 Hz), 3.93 (s, 3H), 3.99-3.39 (m, 8H). $^{13}C$ NMR (500 MHz, $CDCl_3$): 171.5, 169.6, 167.9, 158.6, 158.3, 153.9, 152.9, 149.7, 136.1, 134.5, 133.7, 132.4, 130.6, 129.0, 128.9, 127.2, 127.2, 120.4, 116.0, 115.7, 115.0, 113.7, 109.6, 109.4, 104.1, 103.9, 56.1, 37.4. IR $\nu_{max}$ 3434, 2360, 2095, 1645, 1517, 1432, 1272, 1206, 1147, 916. HRMS (ESI) m/z 591.2265 [calcd for $C_{34}H_{30}N_4O_6$ $(M+H)^+$ 591.2244]

Example 4: Synthesis of S4

A. Preparation of S2

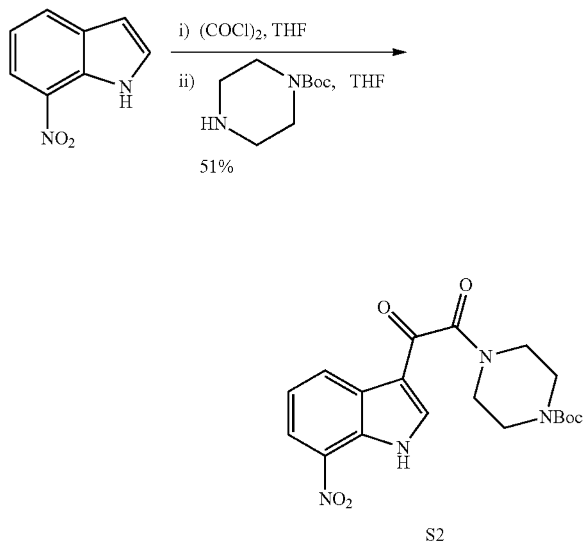

S2

To 7-nitroindole (0.50 g, 3.1 mmol) in THF (8 mL) under $N_2$ at room temperature was added oxalyl chloride (1.4 mL, 15.4 mmol, 5 eq.). After 23 hours the crude reaction mixture was concentrated and redissolved in THF under $N_2$. To this solution was added 1-boc-piperazine (0.69 g, 3.7 mmol, 1.2 eq.) then $NEt_3$ (1.2 mL, 6.16 mmol, 2 eq.). The reaction was allowed to proceed for 24 h. The crude reaction mixture was diluted with $CH_2C_2$ and washed with $NaHCO_3$. The organic layer was dried with $MgSO_4$, decanted, and concentrated. The crude reaction mixture was purified using flash column chromatography ($SiO_2$, 0-100% EtOAc/Hexanes) to afford S2 as a (0.626 g, 51%) yellow solid.

$^1$H NMR (500 MHz, $CDCl_3$) δ 10.56 (s, 1H), 8.76 (d, 1H, J=7.9 Hz), 8.28 (d, 1H, J=8.1 Hz), 8.21 (d, 1H, J=3.1 Hz), 7.47 (app. t, 1H, J=8.0 Hz), 3.75 (m, 2H), 3.58 (m, 2H), 3.55-3.47 (m, 4H). $^{13}$C NMR (500 MHz, $CDCl_3$): 185.3, 165.3, 154.6, 137.0, 133.6, 130.5, 129.8, 128.8, 123.1, 121.2, 115.7, 80.8, 46.2, 41.8, 28.5. IR $\nu_{max}$ 3273, 2976, 1699, 1634, 1532, 1485, 1412, 1364, 1332, 1302, 1286, 1249, 1166, 1125, 1063, 1035, 995, 974, 928, 863, 810, 795, 772, 734, 659. HRMS (ESI) m/z 425.1255 [calcd for $C_{19}H_{22}N_4O_6$ (M+Na) 425.1437]

B. Preparation of S3

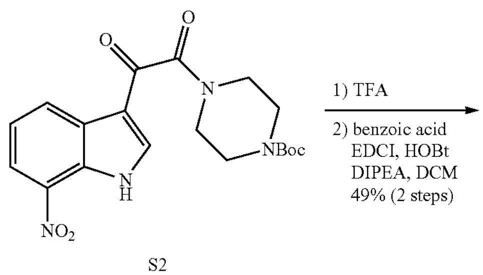

S2

-continued

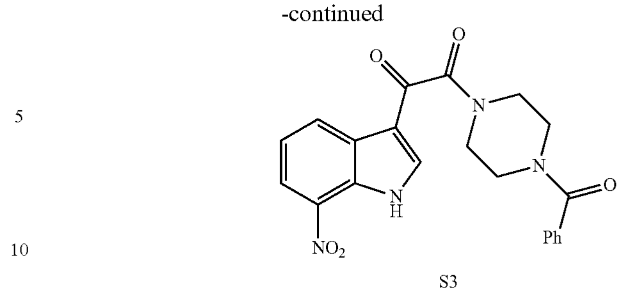

S3

To a solution of S2 (0.386 g, 0.959 mmol) in $CH_2Cl_2$ (6.5 mL) was added TFA (1.5 mL, 1.5 mL/mmol). After four hours, no starting material was observed by LC/MS. The reaction mixture was concentrated repeatedly with $CH_2Cl_2$. The crude product was then put under $N_2$ atmosphere and dissolved in CH$_2$Cl2 (10 mL). To this solution was added benzoic acid (0.129 g, 1.05 mmol, 1.1 eq.), EDCI·HCl (0.203 g, 1.05 mmol, 1.1 eq.), and HOBt·$H_2O$ (0.142 g, 1.05 mmol, 1.1 eq). After 25 minutes $NEt_3$ was added and to the reaction mixture, and the reaction was allowed to proceed overnight. The crude reaction mixture was washed with $NaHCO_3$ then $NH_4Cl$. The organic layer was dried with $MgSO_4$, decanted, and concentrated. The crude reaction mixture was purified using flash column chromatography ($SiO_2$, 50% EtOAc/Hexanes—10% MeOH/EtOAc) to afford S3 as a (186 mg, 49%) yellow solid.

$^1$H NMR (500 MHz, $CDCl_3$) δ 10.58 (s, 1H), 8.74 (s, 1H), 8.27 (d, 1H, J=8.1 Hz), 8.23 (d, 1H, J=2.9 Hz), 7.45 (m, 6H), 4.08-3.41 (m, 8H). $^{13}$C NMR (500 MHz, $CDCl_3$): 185.0, 170.9, 165.2, 137.2, 135.0, 133.6, 130.4, 129.8, 128.9, 128.8, 127.2, 123.2, 121.3, 115.6, 42.1, 29.9. IR $\nu_{max}$ 3449, 2925, 2854, 1741, 1631, 1532, 1438, 1369, 1333, 1251, 1116, 1050, 975, 792, 736, 440, 425, 410. HRMS (ESI) m/z 407.1341 [calcd for $C_{21}H_{18}N_4O_5$ (M+H) 407.1355]

C. Preparation of S4

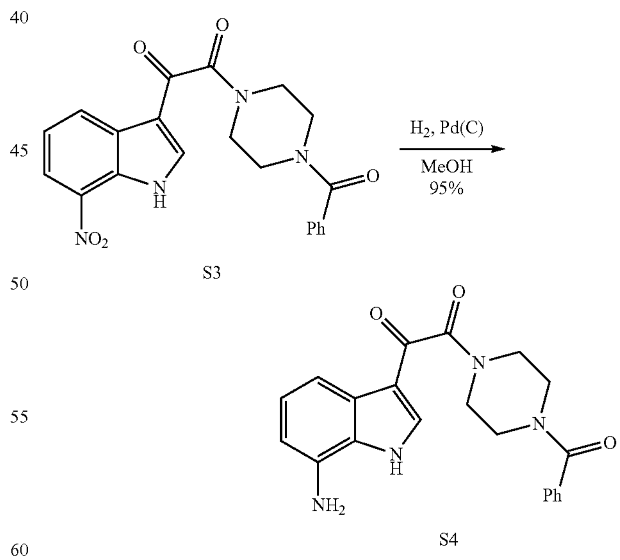

S3

S4

To a solution of S3 (0.186 g, 0.458 mmol) in methanol (10 mL) under $N_2$ was added Pd/C (0.010 g). $H_2$ gas was then bubbled into the solution and the reaction was allowed to stir overnight. The crude reaction mixture was filtered through sand and concentrated to afford S4 (163 mg, 95%) as an olive green solid.

$^1H$ NMR (500 MHz, $CDCl_3$) δ 10.89 (s, 1H), 7.64 (app. s, 1H), 7.40 (m, 6H), 7.07 (t, 1H, J=7.7 Hz), 6.56 (d, 1H, J=7.6 Hz), 3.49 (s, 2H), 3.94-3.32 (m, 8H). $^{13}C$ NMR (500 MHz, $CDCl_3$): 185.0, 171.0, 167.2, 135.2, 134.8, 132.8, 130.5, 129.8, 128.9, 127.2, 127.0, 126.3, 124.7, 114.6, 112.1, 110.2, 51.0, 46.3, 41.7. IR $\nu_{max}$ 3583, 3366, 3237, 2914, 1717, 1621, 1522, 1434, 1251, 1158, 1003, 427. HRMS (ESI) m/z 377.1600 [calcd for $C_{21}H_{20}N_4O_3$(M+H)$^+$ 377.1614]

Example 5: Synthesis of AEG-III-087

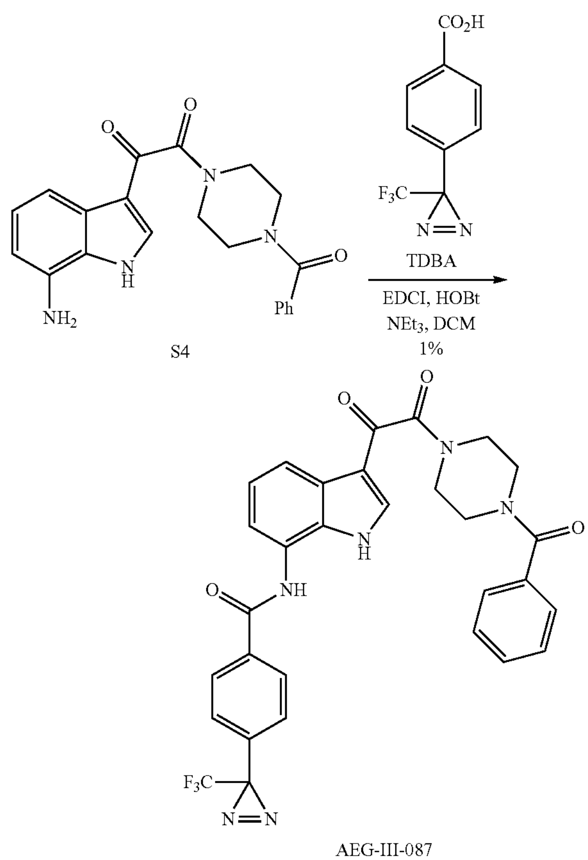

S4

AEG-III-087

To a solution of S4 (0.156 g, 0.414 mmol), TDBA (0.143 g, 0.622 mmol, 1.5 eq.), EDCI·HCl (0.119 g, 0.622 mmol, 1.5 eq.), and HOBt·$H_2O$ (0.095 g, 0.622 mmol, 1.5 eq.) in $CH_2Cl_2$ (18.4 mL) in a round bottom flask shielded from light under $N_2$ was added $NEt_3$ (0.11 mL, 0.828 mmol, 2 eq.). After 18 h, the crude reaction material was concentrated, dissolved in 1:1 ACN/$H_2O$ and purified using reverse phase HPLC (15 mL/min 20-95% ACN/$H_2O$+0.1% TFA, 15 min) to afford AEG-III-087 as a green-yellow solid (3.4 mg, 1.4%).

$^1H$ NMR (500 MHz, $CDCl_3$) δ 9.10 (s, 1H), 8.10 (s, 1H), 8.00 (d, 2H, J=8.1 Hz), 7.64 (s, 1H), 7.43 (m, 5H), 7.30 (d, 2H, J=8.1 Hz), 7.20 (m, 1H), 7.01 (d, 1H, J=7.6 Hz), 4.02-3.33 (m, 8H). $^{13}C$ NMR (500 MHz, $CDCl_3$): 184.9, 171.3, 166.7, 165.2, 135.6, 134.7, 134.5, 133.5, 130.6, 130.5, 128.9, 128.7, 128.2, 127.7, 127.2, 126.9, 126.5, 123.6, 123.1, 122.9, 120.9, 119.9, 116.8, 114.2, 41.8, 29.9, 28.7, 28.4, 28.0. IR $\nu_{max}$ 3281, 2923, 2861, 1784, 1717, 1627, 1429, 1250, 1156, 999, 939, 440, 425, 409. HRMS (ESI) m/z 589.1798 [calcd for $C_{30}H_{23}F_3N_6O_4$ (M+H)$^+$ 589.1811]

Example 6: Synthesis of AEG-III-095

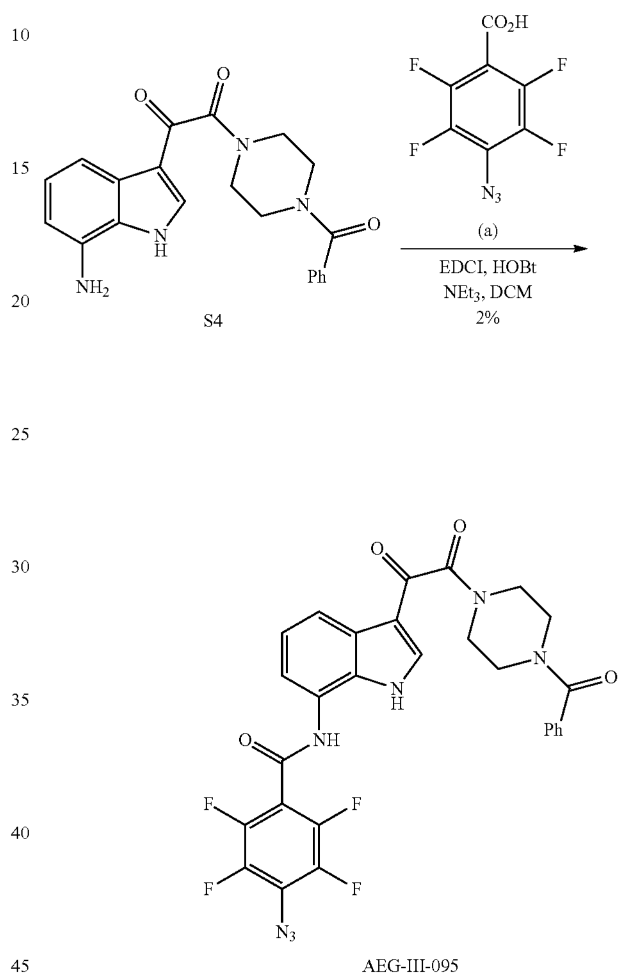

S4

AEG-III-095

To a solution of (a) (0.024 g, 0.10 mmol, 1.5 eq.) in $CH_2Cl_2$ (4 mL) in a round bottom flask shielded from light under $N_2$ at 0° C. was added EDCI·HCl (0.016 g, 0.010 mmol, 1.5 eq.), HOBt·$H_2O$ (0.015 g, 0.10 mmol, 1.5 eq.), $NEt_3$ (0.02 mL, 0.13 mmol, 2 eq.), then S4 (0.025 g, 0.066 mmol). The reaction mixture was allowed to gradually warm to room temperature overnight. The crude reaction mixture was concentrated, dissolved in 1:1 ACN/$H_2O$, and purified using reverse phase HPLC (15 mL/min 20-95% ACN/$H_2O$+ 0.1% TFA, 15 min) to afford AEG-III-095 as a green-yellow solid (0.68 mg, 2%).

$^1H$ NMR (500 MHz, $CDCl_3$) δ 10.47 (s, 1H), 8.80 (s, 1H), 8.24 (s, 1H), 7.81 (s, 1H), 7.45 (m, 5H), 6.96 (d, 1H, J=7.6 Hz), 4.03-3.40 (m, 8H). $^{13}C$ NMR (500 MHz, $CDCl_3$): 184.7, 171.0, 166.4, 156.3, 135.5, 134.5, 130.4, 128.8, 128.1, 127.8, 127.1, 123.5, 121.8, 120.5, 116.4, 114.3, 29.7. IR $\nu_{max}$ 3265, 2359, 2127, 1634, 1486, 1422, 1257, 1157, 999, 912, 731, 668. HRMS (ESI) m/z 594.1520 [calcd for $C_{28}H_{19}F_4N_7O_4$ (M+H)$^+$594.1513].

Example 7: Synthesis of AEG-III-096

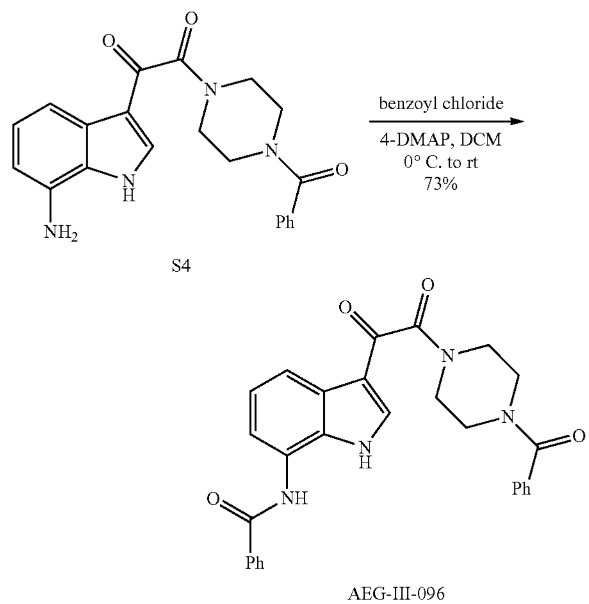

S4

AEG-III-096

To a solution of S4 (0.044 g, 0.12 mmol) in $CH_2Cl_2$ (2.5 mL) under $N_2$ at 0° C. was added benzoyl chloride (0.049 g, 0.35 mmol, 3 eq.), then 4-DMAP (0.043 g, 0.35 mmol, 3 eq.). The reaction mixture was allowed to gradually warm to room temperature overnight. After 15 h, the crude reaction mixture was purified using flash column chromatography ($SiO_2$, 0-100% EtOAc/Hex) to afford AEG-III-096 (0.041 g, 73%) as a white solid.

$^1H$ NMR (500 MHz, $CDCl_3$) δ 11.07 (s, 1H), 8.95 (s, 1H), 8.10 (s, 1H), 7.96 (d, 1H, J=7.6 Hz), 7.70 (s, 1H), 7.58 (t, 1H, J=7.5 Hz), 7.40 (m, 5H), 7.18 (app. s, 1H), 7.06 (d, 1H), J=7.51 Hz), 3.93-3.29 (m, 8H). $^{13}C$ NMR (500 MHz, $CDCl_3$): 185.1, 170.9, 166.6, 166.4, 135.6, 135.0, 133.8, 132.5, 130.4, 129.0, 128.9, 128.8, 127.7, 127.2, 123.5, 123.4, 119.5, 116.6, 114.4, 29.9. IR $\nu_{max}$ 3283, 1629, 1528, 1425, 1251, 1157, 998, 710, 427. HRMS (ESI) m/z 481.1876 [calcd for $C_{28}H_{24}N_4O_4$ $(M+H)^+$ 481.1876]

Example 8: Assays

Envelope glycoprotein constructs: The HIV-$1_{JR-FL}$ Env and HIV-$1_{AD8}$ mutant Envs were coexpressed in HOS cells with the Rev protein by the pSVIIIenv expression vector, using the natural HIV-1 env and rev sequences. The HIV-$1_{AD8}$ env mutations were introduced by site-directed mutagenesis PCR using Pfu Ultra II polymerase (Agilent Technologies) or the Q5 site-directed mutagenesis kit (NEB), following the manufacturer's protocol. The plasmids for the expression of HIV-1 virions with the HIV-$1_{JR-FL}$ Env used for single-molecule FRET are described in Munro, Science 346, 759-763 (2014). The wild-type HIV-$1_{AD8}$ and HIV-$1_{CH848}$ Envs were expressed in A549 cells using a lentivirus vector, as described below.

Antibodies: Antibodies against HIV-1 Env were kindly supplied by Dr. Dennis Burton (Scripps), Drs. Peter Kwong and John Mascola (Vaccine Research Center, NIH), Dr. Barton Haynes (Duke), Dr. Michel Nussenzweig (Rockefeller), Dr. Hermann Katinger (Polymun), Dr. James Robinson (Tulane) and Dr. Marshall Posner (Mount Sinai Medical Center). In some cases, anti-Env antibodies were obtained through the NIH AIDS Reagent Program. Antibodies for Western blotting include goat anti-gp120 polyclonal antibody (ThermoFisher), the 4E10 anti-gp41 antibody (Polymun), and anti-Gag p55/p24/p17 (Abcam). An HRP-conjugated rabbit anti-goat IgG antibody (ThermoFisher) or HRP-conjugated goat anti-human IgG (Santa Cruz) were used as secondary antibodies for Western blotting.

Cell lines: 293T cells (ATCC) were grown in DMEM supplemented with 10% fetal bovine serum (FBS) and 100 μg/ml of penicillin-streptomycin. Cf2Th-CD4/CCR5 cells stably expressing the human CD4 and CCR5 coreceptors for HIV-1 were grown in the same medium supplemented with 0.4 mg/ml of G418 and 0.2 mg/ml of hygromycin. HOS cells (ATCC) were grown in DMEM with 5% FBS and 100 μg/ml of penicillin-streptomycin. The A549 lung epithelial cells (ATCC) were grown in DMEM/F12, 10% FBS supplemented with L-glutamine and penicillin-streptomycin. All cell culture reagents are from Life Technologies.

Human A549 cells inducibly expressing Env or Env on virus-like particles (VLPs) were established. A549 cells constitutively expressing the reverse tet transactivator were transduced with an HIV-1-based lentivirus vector expressing Rev and Env from HIV-$1_{AD8}$, a primary HIV-1 strain. The vector transcribes a bicistronic mRNA comprising HIV-$1_{AD8}$ rev and env and two selectable marker genes (puromycin-T2A-enhanced green fluorescent protein (EGFP)) fused in-frame with a T2A peptide-coding sequence. In the transduced cells, Env expression is controlled by the Tet-Responsive Element (TRE) promoter and tet-on transcriptional regulatory elements. Env-expressing cells were enriched by doxycycline induction and fluorescence-activated cell sorting for the coexpressed EGFP marker. Approximately 72 hours after treatment of these cells with 2 μg/ml doxycycline, the HIV-$1_{AD8}$ gp160 Env precursor and the mature gp120 and gp41 glycoproteins were expressed. Herein, these cells are designed as A549-Env.

To produce cells expressing Env and VLPs, the A549-Env cells were transduced with a lentivirus vector expressing the HIV-1 Gag precursor fused with mCherry. The doxycycline-regulated expression of the Gag-mCherry fusion protein resulted in the release of Env-containing VLPs into the medium. Herein, these cells are designated as A549-Gag/Env.

Immunoprecipitation of cell-surface Env: Doxycycline-induced A549-Env cells were washed twice with washing buffer (1×PBS+5% FBS), with or without 10 μM BMS-806 or compounds described herein. The cells were then incubated with 5 μg/ml antibody for one hour at 4° C. in the continued presence or absence of the compounds described herein. After washing four times in washing buffer, the cells were lysed in NP-40 lysis buffer (0.5% NP-40, 0.5 M NaCl, 10 mM Tris, pH 7.5) for five minutes at 4° C. with gentle agitation. Unless specifically indicated otherwise, compounds described herein were not added to the NP-40 lysis buffer. The lysates were cleared by centrifugation at 13,200×g for 20 minutes at 4° C., and the clarified supernatants were incubated with Protein A-Sepharose beads (50 μl of 25 mg/ml in PBS per sample) for one hour at room temperature. The beads were pelleted (1000 rpm×1 min) and washed three times with final wash buffer (200 mM Tris-HCl, pH 8.0, 100 mM $(NH_4)_2SO_4$, 1 M NaCl and 0.1% NP-40). The beads were suspended in LDS sample buffer, boiled and analyzed by Western blotting using 1:2000 goat anti-gp120 polyclonal antibody (ThermoFisher) and 1:2000 HRP-conjugated rabbit anti-goat IgG (ThermoFisher). The transmembrane Env was analyzed by Western blot with the 4E10 anti-gp41 antibody and HRP-conjugated goat anti-human IgG (Santa Cruz).

For analysis of total Env expression in the cell, some of the clarified lysates were saved before the addition of Protein A-Sepharose beads and Western blotted as described above.

Antibody recognition of monomeric gp120: To produce gp120 monomers, a stop codon was introduced into the HIV-$1_{AD8}$ env gene sequence encoding the gp120-gp41 junction. Transfection of 293F cells with this plasmid DNA resulted in the transient expression of a secreted, monomeric gp120 glycoprotein into cell supernatants. The supernatants were clarified by low-speed centrifugation and 0.45-μ filtration, and then used for precipitation by antibodies in the absence or presence of 10 μM BMS-806. Precipitates were Western blotted with a goat anti-gp120 polyclonal antibody (ThermoFisher) and 1:3000 HRP-conjugated rabbit anti-goat IgG antibody (ThermoFisher).

Characterization of VLP-associated Env: To prepare VLPs with HIV-$1_{AD8}$ Env, 150-mm dishes of 30-40% confluent A549-Gag/Env cells were seeded and, on the following day, treated with 2 μg/ml doxycycline. Approximately 72 hours after induction, cell supernatants were harvested and cleared by low-speed centrifugation (500×g for 15 minutes at 4° C.) and 0.45-μ filtration. VLPs were pelleted by centrifugation at 100,000×g for one hour at 4° C. The resuspended VLP preparation was clarified by low-speed centrifugation. BMS-806 and compounds described herein were added to the clarified VLP-containing suspensions. In some cases, the VLP-compound mixtures were irradiated with a 100-watt, 365-nm ultraviolet (UV) lamp for 10 minutes at room temperature. For all UV studies, exposure of the samples to visible light was minimized.

For studies of the reversibility of effects, the compounds were added to the VLPs and mixed for several seconds at room temperature. Then the VLPs were pelleted (20,000×g for 30 minutes at 4° C.) twice, washing with 1.5 ml PBS with 2% DMSO. The pelleted VLPs were resuspended in 1 ml PBS with 2% DMSO and incubated at room temperature for various lengths of time (20 minutes—3 weeks). Control VLPs were incubated in the continued presence of the compounds at room temperature for the same length of time. Then the VLPs were pelleted (20,000×g for 30 minutes at 4° C.) and the pellet incubated with 1.5% Triton X-100 for 30 minutes at 4° C. The VLP lysates were centrifuged (20, 000×g for 30 minutes at 4° C.) and the supernatants were incubated with antibodies (10 μg/ml) in a 50-μl volume with 25 mg/ml of Protein A-Sepharose beads for one hour at 4° C. The beads were pelleted (1000 rpm for 1 minute at room temperature) and washed three times with 1 ml wash buffer with 1% Triton X-100. The beads were suspended in NuPAGE LDS Sample Buffer (ThermoFisher), boiled and analyzed by Western blot, as described above.

For studies of the binding of ligands (antibodies, CD4-Ig and C34-Ig) to detergent-solubilized VLP Env, VLPs prepared as described above were pelleted (20,000×g for 30 minutes at 4° C.). The pellet was incubated with 1.5% Triton X-100 for 30 minutes at 4° C. The VLP lysates were centrifuged (20,000×g for 30 minutes at 4° C.) and the supernatants were incubated with ligands (10 μg/ml) in a 50-μl volume with 25 mg/ml of Protein A-Sepharose beads for one hour at 4° C. The beads were pelleted (1000 rpm for 1 minute at room temperature), washed three times with 1 ml wash buffer with 1% Triton X-100, suspended in LDS Sample Buffer and analyzed by Western blot, as described above.

In a second assay format, the effect of the compounds was analyzed on the binding of antibodies to Env on intact VLPs, in the absence of detergent. In this case, VLPs in A549-Gag/Env supernatants, clarified as described above, were pelleted at 100,000×g for one hour at 4° C. The pellet was resuspended in PBS and the VLPs pelleted at 20,000×g for 30 minutes at 4° C. The VLPs were resuspended in PBS and incubated with antibodies (10 μg/ml) in a 100-μl volume for one hour at 4° C. The VLPs were then pelleted (20,000×g for 30 minutes at 4° C.) and washed with PBS three times. The VLP pellet was then solubilized in 1.5% Triton X-100 for 30 minutes at 4° C., after which the VLP lysates were clarified by centrifugation at 20,000×g for 30 minutes at 4° C. The supernatants were incubated with 50 μl of Protein A-Sepharose beads for one hour at 4° C. The beads were pelleted (1000 rpm for 1 minute at room temperature), washed three times with 1 ml wash buffer with 1% Triton X-100, suspended in LDS Sample Buffer, and analyzed by Western blot, as described above.

Association of gp120 with Env complexes: The non-covalent association of gp120 with HIV-1 Env complexes was studied using carboxy-terminally His6-tagged Envs from three different sources: 1) VLPs produced from A549-Gag/Env cells; 2) A549 cells expressing HIV-$1_{AD8}$ and HIV-$1_{CH848}$ Envs; and 3) HOS cells transiently expressing wild-type HIV-$1_{JR-FL}$ Env and wild-type and mutant HIV-$1_{AD8}$ Envs. VLP and cell lysates from A549 cells were prepared in 1.5% Triton X-100. Cell lysates from HOS cells were prepared in 1.5% Cymal-5 (Anatrace). The VLP and cell lysates were clarified as described above. DMSO, a compound described herein, sCD4 or the CD4-mimetic compound, BNM-III-170 (Melillo, ACS Med Chem Letters 7, 33-334, 2016), was added to the lysate. Aliquots of the lysates were saved for Western blotting to detect the gp160, gp120 and gp41 glycoproteins in the input sample. The bulk of the lysates was incubated with nickel-nitriloacetic acid (Ni-NTA) beads (Qiagen) for 1.5 hours at 4° C. The beads were pelleted (1000 rpm for 1 minute at room temperature), washed 3 times with wash buffer with 1% Triton X-100, boiled in LDS sample buffer, and analyzed by Western blotting as described above.

Shedding of gp120 from VLP Env: The effect of compounds on the spontaneous shedding of gp120 from VLP Env was evaluated. VLPs with the wild-type HIV-$1_{AD8}$ Env were prepared from the supernatants of A549-Gag/Env cells, as described above. The VLPs were suspended in PBS, to which was added either DMSO or a compound described herein. An aliquot of the VLP suspension in PBS/DMSO was processed as described below to serve as a Day 0 control. The VLP suspensions were incubated for 4 days at 4° C., room temperature or 37° C. (with gentle rocking). Then the VLPs were pelleted (100,000×g for 30 min at 4° C.). The pellets and supernatants were boiled in LDS sample buffer and analyzed by Western blotting with either 1:2000 goat anti-gp120 polyclonal antibody (ThermoFisher) and HRP-conjugated rabbit anti-goat IgG antibody, or with 1:5000 rabbit anti-Gag p55/p24/p17 antibody (Abcam) and HRP-conjugated goat anti-rabbit IgG antibody (Abcam).

Infection of single-round recombinant viruses: To produce single-round HIV-1 expressing luciferase, 293T human embryonic kidney cells were cotransfected with plasmids expressing the pCMVΔP1Δenv HIV-1 Gag-Pol packaging construct, the HIV-1 envelope glycoproteins or the envelope glycoprotein of the control amphotropic murine leukemia virus (AMLV), and the firefly luciferase-expressing vector at a DNA ratio of 1:1:3 μg using the Effectene transfection reagent (Qiagen) (Madani, J Virol 78, 3742-3752, 2004).

The plasmids expressing the HIV-1 envelope glycoproteins and Rev protein were based on pSVIIIenv or pcDNA3.1 (Invitrogen Life Technologies, Carlsbad, CA). Cotransfection produced recombinant, luciferase-expressing viruses capable of a single round of infection. The virus-containing supernatants were harvested between 36 and 40 h after transfection and cleared of debris by low-speed centrifugation. Aliquots of the virus preparations were frozen at −80° C. until further use. The reverse transcriptase (RT) levels of all virus stocks were measured.

Cf2Th-CD4/CCR5 target cells were seeded at a density of $6\times10^3$ cells/well in 96-well luminometer-compatible tissue culture plates (PerkinElmer) 24 h before infection. On the day of infection, compounds described herein (0-100 nM) were incubated with recombinant viruses (10,000 RT units) at 37° C. for 30 min. The virus-compound mixtures were added to the target cells and incubated for 48 h at 37° C. After this time, the medium was removed from each well and the cells were lysed by the addition of 30 μl passive lysis buffer (Promega) and three freeze-thaw cycles. An EG&G Berthold LB 96 V microplate luminometer was used to measure the luciferase activity in each well after the addition of 100 μl of luciferin buffer (15 mM $MgSO_4$, 15 mM $KPO_4$, pH 7.8, 1 mM ATP, and 1 mM dithiothreitol) and 50 μl of 1 mM 99% Firefly d-luciferin free acid (Prolume).

Single-molecule fluorescence resonance energy transfer (smFRET): Viruses with HIV-$1_{JR\text{-}FL}$ Env that is double-tagged at V1-Q3 and V4-A1 were prepared for smFRET imaging, as described in Munro, Science 346, 759-763 (2014). The high (40:1) ratio of wild-type Env to tagged Env ensures that, on average, only one tagged protomer is available for imaging on a single virus particle. The Q3 and A1 double-tagged viruses allowed the incorporation of Cy3B and Cy5 fluorescent labels, respectively. Thus, the relative movements of the V1 and V4 regions in one gp120 subunit of an individual Env trimer could be monitored in real time. The smFRET images were acquired on an in-house-built total internal reflection fluorescent microscope, as described in Munro. HIV-$1_{JR\text{-}FL}$ viruses incubated with saturating concentrations (100 μM) of AEG-II-168 or control HIV-$1_{JR\text{-}FL}$ viruses without compound were used for smFRET imaging. Data were analyzed with the customized MATLAB (Mathworks) program SPARTAN as described in Juette, Nat Methods 13, 341-344 (2016). FRET trajectories meeting the criteria of quality (sufficient signal:noise ratio, single dye photobleaching, anti-correlated features between donor and acceptor intensity and fluorescence lifetime) were compiled into FRET histograms. Hidden Markov modeling was used to fit the FRET histograms with the sum of three Gaussian distributions. The three-state model yielded the lowest log likelihood value in this case.

Modeling compound interaction with Env: The HIV-$1_{BG505}$ soluble gp140 SOSIP.664 trimer complexed with BMS-529 (PDB 5U7O) was used as a docking target and prepared using Maestro 12.0.012 (Schrodinger 2019). See, Pancera, Nat Chem Biol 13, 1115-1122 (2017). 20 best-ranked poses for BMS-529, AEG-II-168 and AEG-II-159 were determined by Glide (Schrodinger).

Statistical analysis: Statistical analyses were performed using GraphPad Prism 6 (Graph Pad Software).

The Kolmogorov-Smirnov test was used to check the data distribution in FIG. 1. A two-tailed paired Student's t-test or Wilcoxon matched-pairs signed-rank test was used to compare two groups and to determine if the data fitted a normal distribution, respectively.

Pearson's correlation was used to analyze the correlation between groups in FIG. 2.

In all cases a P value less than 0.05 as a cutoff for statistical significance was used.

A. Results (i) Effects of BMS-806 on the Conformation of Cell-Surface Env

The full-length HIV-$1_{AD8}$ Env was inducibly expressed in A549 cells (herein designated A549-Env cells). The efficiency with which Env is proteolytically processed in these cells allows an evaluation of the conformation of both the mature (cleaved) Env and the uncleaved Env. The cell-surface HIV-$1_{AD8}$ Env was precipitated by a panel of Env ligands in the presence of BMS-806 or the DMSO vehicle control (FIG. TA). Recognition of the mature HIV-$1_{AD8}$ gp120 glycoprotein on the cell-surface Env trimer was highly correlated with the ability of gp120 ligands to neutralize HIV-$1_{AD8}$ (FIG. 1B); in the absence of BMS-806, broadly neutralizing antibodies exhibited significantly better gp120 recognition than poorly neutralizing antibodies ($P<0.0008$, two-tailed unpaired t test). This observation suggests that the mature cell-surface Env conformationally resembles the functional virion Env. In the absence of BMS-806, most broadly neutralizing antibodies (bNAbs) recognized the cleaved Env. Some bNAbs (PG9, PG16, PGT145, PGT151 and 35022) directed against quaternary Env epitopes recognized both uncleaved and mature Envs, but exhibited preferential recognition of the cleaved Env. The 2F5, 4E10 and 10E8 bNAbs against the gp41 membrane-proximal external region (MPER) only inefficiently precipitated the gp120 glycoprotein in the absence of BMS-806, although these MPER bNAbs recognized gp41 and the uncleaved gp160 Env efficiently. Poorly neutralizing antibodies preferentially precipitated the uncleaved Env, which samples non-State-1 conformations more readily than the mature Env.

Figure 1B:
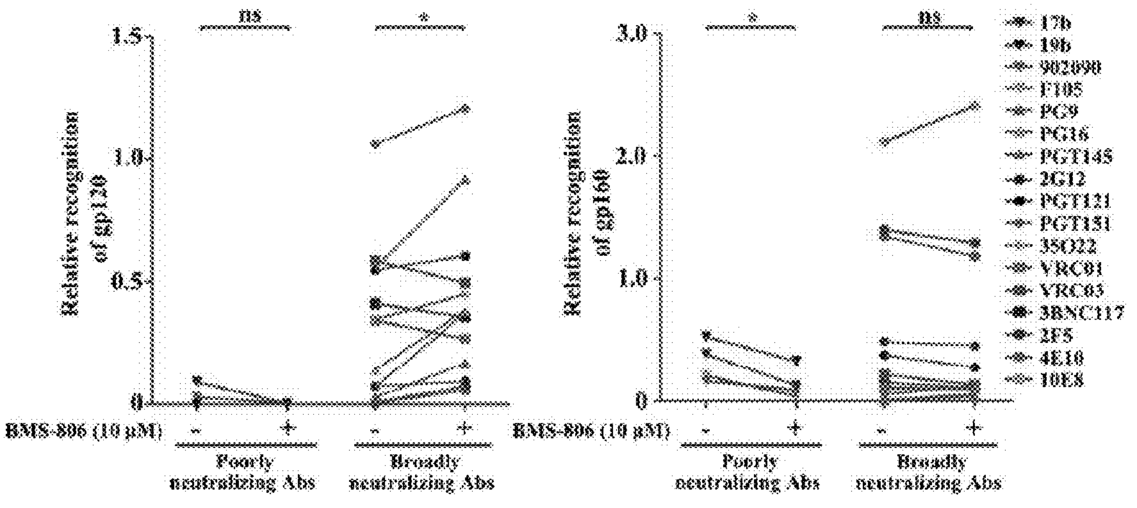

BMS-806 treatment altered Env recognition by several ligands (FIG. 1B). BMS-806 increased the binding of some bNAbs, particularly those against V2 quaternary epitopes (PG9, PG16 and PGT145) and the gpT20-gp4T interface (PGT151 and 35022), to the mature gp120 glycoprotein. The binding of bNAbs (2G12 and PGT121) to glycan-dependent gp120 outer domain epitopes was not affected by incubation with BMS-806. The binding of bNAbs (VRC01, VRC03 and 3BNC117) against the gp120 CD4-binding site (CD4BS) was either unchanged or slightly decreased by BMS-806. BMS-806 decreased the recognition of the uncleaved Env by the poorly neutralizing antibodies (17b, 19b, 902090 and F105).

Figure 10A:
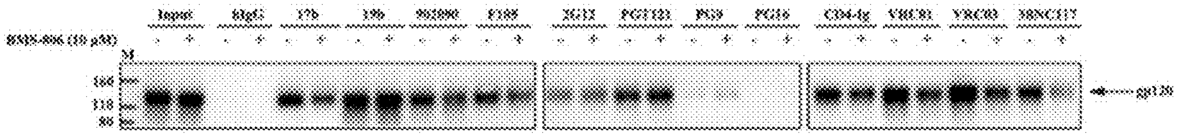
FIGS. 10A-10B show the effect of BMS-806 on antibody recognition of monomeric gp120 and cell-surface Env.

To help interpret the observed BMS-806 effects on ligand binding to cell-surface Env trimers, monomeric soluble HIV-$1_{AD8}$ gp120 was precipitated by Env ligands in the absence and presence of BMS-806 (FIG. 10A). With the exception of the PG9 and PG16 bNAbs, which recognize quaternary V2 epitopes at the Env trimer apex, all of the Env ligands tested efficiently precipitated the monomeric gp120 glycoprotein. BMS-806 mildly decreased gp120 binding of CD4-Ig, several CD4BS bNAbs, and the 17b antibody against a CD4-induced (CD4i) epitope. The very weak binding of the PG9 antibody against a V2 quaternary gp120 epitope to monomeric gp120 was slightly increased by BMS-806. These observations indicate that some of the consequences of BMS-806 on cell-surface Env recognition by CD4BS and CD4i antibodies involve local effects within a gp120 subunit; this interpretation is consistent with the proximity of the BMS-806 binding site to these gp120 epitopes.

Many of the observed effects of BMS-806 on the binding of antibodies, particularly those (PG16, PGT145, PGT151 and 35022) recognizing epitopes dependent on Env quaternary structure, likely involve interactions that occur in the context of the Env trimer. In the presence of BMS-806, the mature cell-surface Env maintained a high level of recognition by bNAbs and a low level of recognition by poorly neutralizing antibodies, consistent with the pattern expected for a functional State-1 Env trimer (FIG. 1B). These results corroborate single-molecule fluorescence resonance energy transfer (smFRET) data indicating that HIV-1 membrane Envs incubated with compounds described herein maintain a State-1-like conformation of gp120. Based on diminished recognition by poorly neutralizing antibodies, the sampling of non-State-1 conformations by the uncleaved Env on the cell surface appears to be decreased in the presence of BMS-806.

Figure 1C:
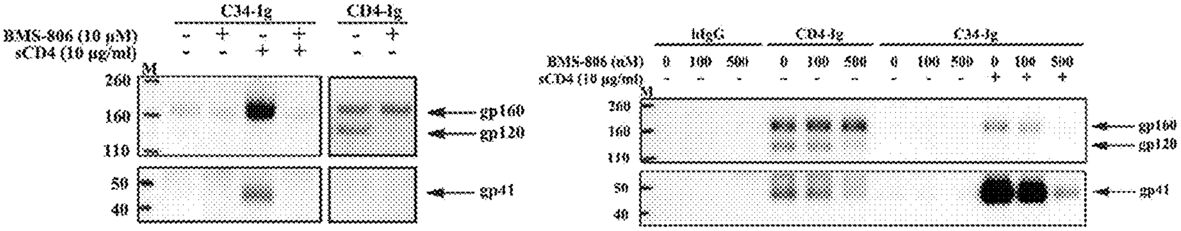

The effect of BMS-806 on the recognition of the cell-surface HIV-$1_{AD8}$ Env by CD4-Ig and C34-Ig was evaluated. CD4-Ig is a soluble CD4-immunoglobulin fusion protein, and C34-Ig contains the gp41 HR2 region fused to an immunoglobulin Fc. C34-Ig efficiently recognized the cell-surface Env only after incubation with soluble CD4 (sCD4) (FIG. 1C, left panel). BMS-806 blocked C34-Ig recognition of Env in the presence of sCD4. At a high concentration (10 μM), BMS-806 inhibited CD4-Ig recognition of the gp120 glycoprotein on the mature Env, but not the uncleaved gp160 Env (FIG. 1C, middle panel). Titration of different concentrations of BMS-806 suggested that C34-Ig binding to Env was inhibited almost completely at 500 nM (FIG. 1C, right panel); at this concentration, CD4-Ig binding to the gp120 and gp160 Envs was still detected. These results verify that BMS-806 blocks CD4-induced conformational changes in Env; at higher concentrations, BMS-806 decreases CD4 binding, more for the cleaved Env than the uncleaved Env.

(ii) Effects of BMS-806 on the Conformation of Env on Virus-Like Particles

To produce virus-like particles (VLPs), the A549-Env cells expressing HIV-$1_{AD8}$ Env were transduced with a lentivirus vector encoding an HIV-1 Gag-mCherry fusion protein. The Gag-mCherry protein produces non-infectious VLPs with an immature core morphology. Filtration and low-speed centrifugation of the A549 cell supernatants removed any significant levels of contaminating Env-containing cellular vesicles; parallel treatment of the A549-Env and the A549-Gag/Env cell supernatants demonstrated that Env could be detected in pellets prepared from the latter cells, but not the former cells. Both mature and uncleaved Envs were incorporated into VLPs (see Input in FIGS. 2A and 2C).

Figure 2A:
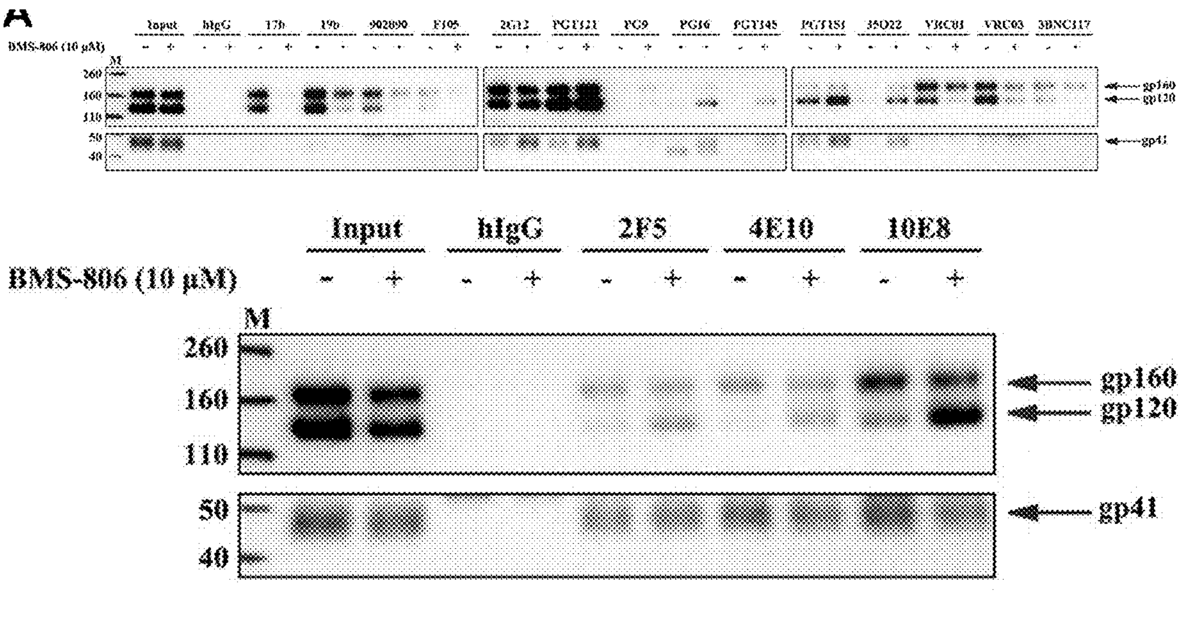
FIGS. 2A-2D show the effect of BMS-806 on the conformation of VLP Env.
Figure 2B:
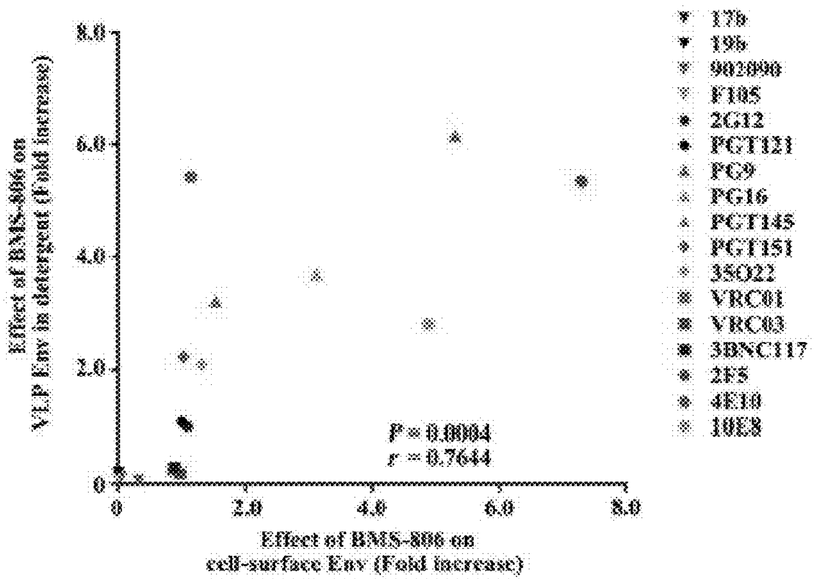
Figure 2C:
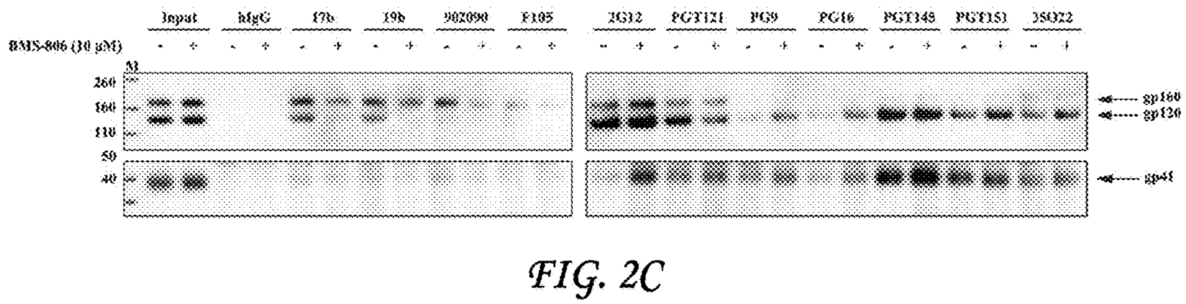
Figure 2D:
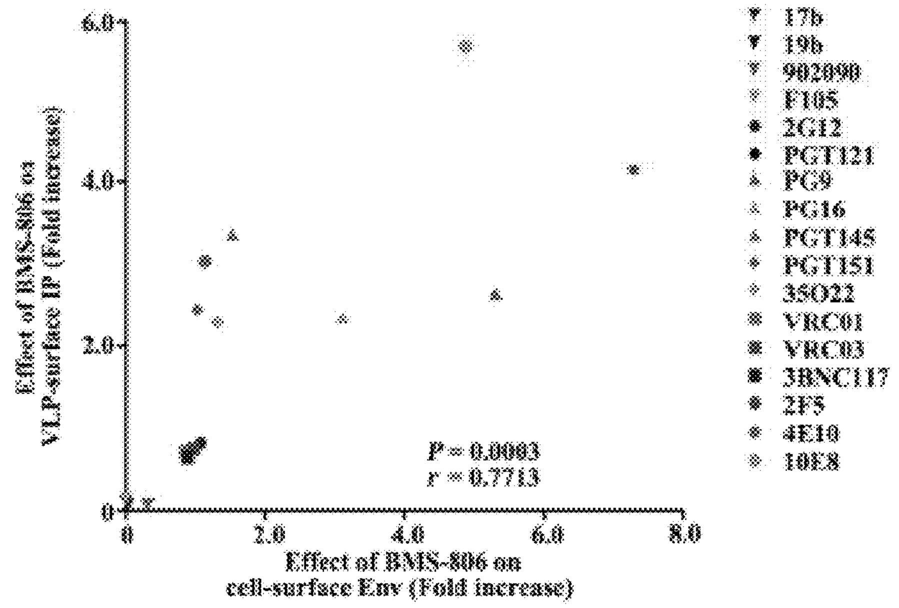
Figure 11:
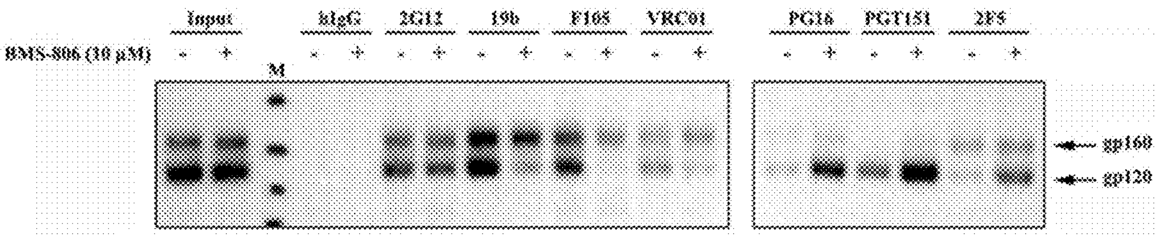
FIG. 11 shows the effect of BMS-806 on the conformation of VLP Env solubilized in Cymal-5. VLPs prepared from A549-Gag/Env cell supernatants were solubilized in 1.5% Cymal-5 and precipitated with the indicated antibodies in the absence or presence of BMS-806. Precipitates of the HIV-$1_{AD8}$ Env were Western blotted with a rabbit anti-gp120 antiserum. M=markers (260, 160, 110 and 80 kDa).

The recognition of the VLP HIV-$1_{AD8}$ Env by a panel of Env ligands was evaluated in the presence of BMS-806 or the control DMSO. In one assay format, the VLPs were solubilized in detergent (Triton X-100 or Cymal 5) before incubation with Env ligands (FIGS. 2A and 11). In a second assay format, the VLPs were pre-incubated with Env ligands in the absence of detergent; the VLPs were then pelleted and washed prior to solubilization in detergent and precipitation of the bound Envs with Protein A-Sepharose beads (FIG. 2C). The results of the two assays were similar except that Env recognition by the quaternary V2 bNAbs (PG9, PG16 and PGT145) was less efficient for the detergent-solubilized VLPs; moreover, without BMS-806 treatment, the recognition of the mature Env on the detergent-solubilized VLPs was slightly greater for the poorly neutralizing antibodies (the 19b anti-V3 antibody, the 17b antibody against a CD4-induced gp120 epitope and the 902090 antibody against a linear V2 gp120 epitope). In the absence of BMS-806, all of the bNAbs recognized the mature Env on intact, detergent-free VLPs to varying degrees (FIG. 2C). BMS-806 enhanced the recognition of the mature gp120 Env by bNAbs (PG9, PG16, PGT145, PGT151 and 35O22) directed against Env epitopes dependent on quaternary conformation. In the presence of BMS-806, precipitation of gp120 by the bNAbs (2F5, 4E10 and 10E8) directed against the gp41 MPER was more efficient. BMS-806 reduced recognition of the uncleaved Env by the poorly neutralizing antibodies, and nearly eliminated the binding of the 19b and 17b antibodies to the mature gp120 Env. The effects of BMS-806 on antibody recognition of gp120 on both solubilized and intact VLPs were directly correlated with the effects of BMS-806 on antibody recognition of cell-surface gp120 Env (FIGS. 2B and 2D). BMS-806 binding appears to be compatible with maintenance of a State-1-like conformation of the mature VLP-associated Env.

(iii) Effect of BMS-806 on Gp120 Association with Env Complexes

Figure 10B:
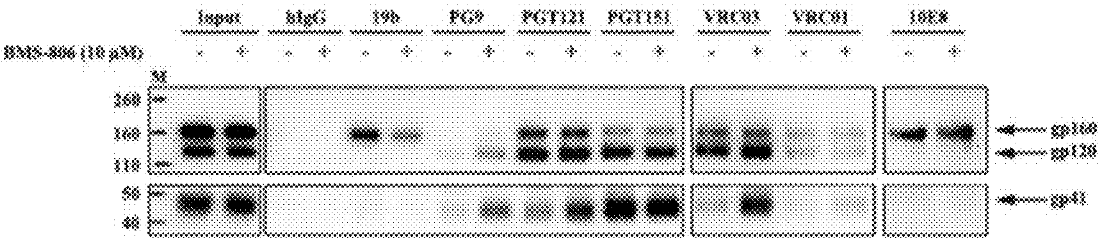

In the cell-surface and VLP Env recognition assays, BMS-806 enhanced the coprecipitation of gp41 by an anti-gp120 antibody or the coprecipitation of gp120 by an anti-gp41 antibody. For example, precipitation of cell-surface Env by the PGT121, VRC01 and VRC03 bNAbs yielded more gp41 in the presence of BMS-806, even though recognition of gp120 was not increased (FIG. 1A). This increased coprecipitation of gp41 by some anti-gp120 bNAbs in a cell-surface Env immunoprecipitation assay was reproduced where BMS-806 was present only prior to cell lysis (FIG. 10B). Conversely, in the presence of BMS-806, more gp120 was precipitated by the 2F5, 4E10 and 10E8 bNAbs against the gp41 MPER, even though BMS-806 did not increase the amount of precipitated gp41 (FIGS. 2A and 2C).

Figure 3A:
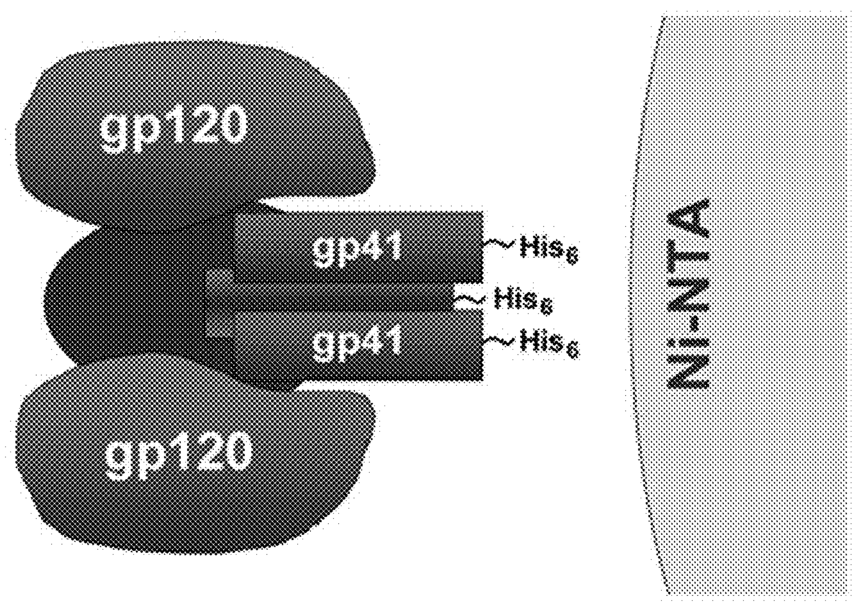
FIGS. 3A-3D show BMS-806 stabilization of gp120 association with Env complexes.
Figure 3B:
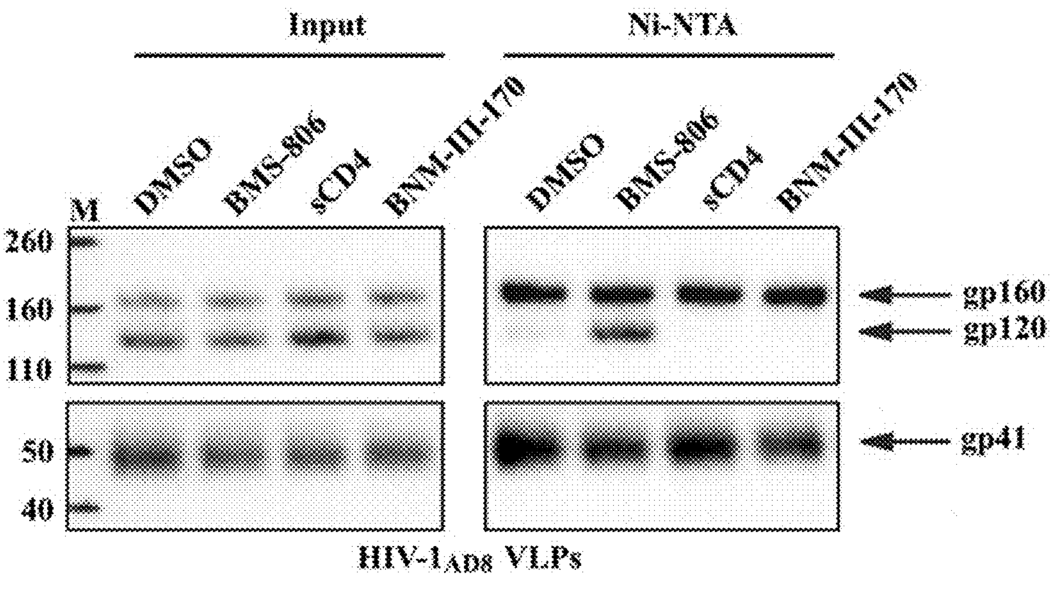
Figure 3C:
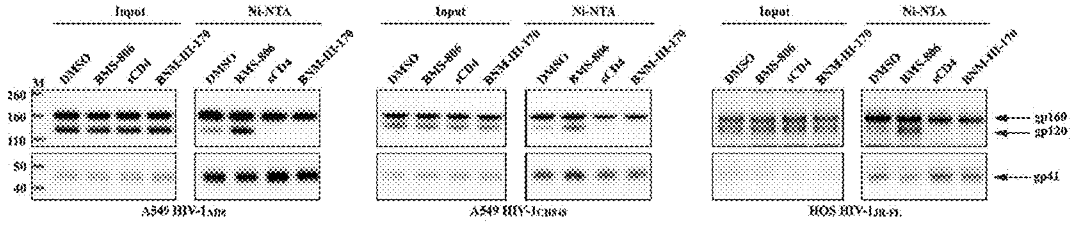

The His6 tag was then used on the gp41 C-terminus to precipitate Env from detergent lysates of VLPs or cells expressing Env (FIG. 3A). The precipitates were then Western blotted with antibodies against gp120 and gp41. When the DMSO control was added to the lysates of VLPs prepared from A549 cells expressing HIV-$1_{AD8}$ Env and Gag-mCherry, both gp160 and gp41 were efficiently precipitated by the Ni-NTA beads; however, little gp120 was coprecipitated with gp41 under these conditions (FIG. 3B). Addition of BMS-806 to the VLP lysates increased the amount of coprecipitated gp120. Addition of sCD4 or the small-molecule CD4-mimetic compound, BNM-III-170, decreased even the small amount of gp120 coprecipitated in the presence of DMSO, suggesting that these ligands induced shedding of gp120, as expected. In assays examining Envs from different HIV-1 strains in cell lysates, BMS-806 increased the amount of coprecipitated gp120, whereas sCD4 and BNM-III-170 decreased the amount of coprecipitated gp120 (FIG. 3C). Consistent with the ability of BMS-806 to interfere with CD4 binding and CD4-induced Env conformational changes, the sCD4-induced shedding of gp120 from the Env complexes could be blocked by the addition of 10 μM BMS-806 to the cell lysates. Thus, BMS-806 may stabilize gp120 association with detergent-solubilized Env complexes.

(iv) Effects of Env Changes on BMS-806 Stabilization of Gp120-Env Association

Figure 3D:
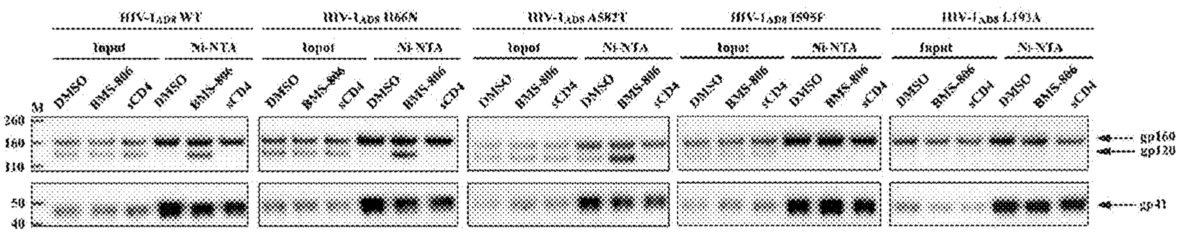

The effects of changes in Env on BMS-806 stabilization of gp120 association with the Env complex were evaluated (FIG. 3D). The H66N change in the gp120 inner domain Layer 1 increases the CD4-off-rate and destabilizes Env conformations downstream of State 1. The A582T change is thought to enhance interactions that maintain the State-1 conformation. Consistent with their predicted occupancy of State 1, the H66N and A582T mutants exhibited a BMS-806-induced increase in gp120-Env association similar to that seen for the wild-type HIV-$1_{AD8}$ Env. By contrast, the I559F change, which decreases HIV-1 sensitivity to compounds described herein, abrogated responsiveness to BMS-806. A similar result was seen for the L193A change in the gp120 V2 region, which predisposes HIV-1 Env to assume State 2/3 conformations and decreases HIV-1 sensitivity to BMS-806. The low basal level of gp120 association with the solubilized HIV-$1_{AD8}$ L193A Env complex may have contributed to its poor responsiveness to BMS-806 in this assay. In summary, some Env changes affecting HIV-1 susceptibility to compounds described herein also influence the BMS-806-induced enhancement of gp120 association with Env complexes.

(v) Reversibility of BMS-806 and BMS-529 Binding to VLP Env

Figure 4:
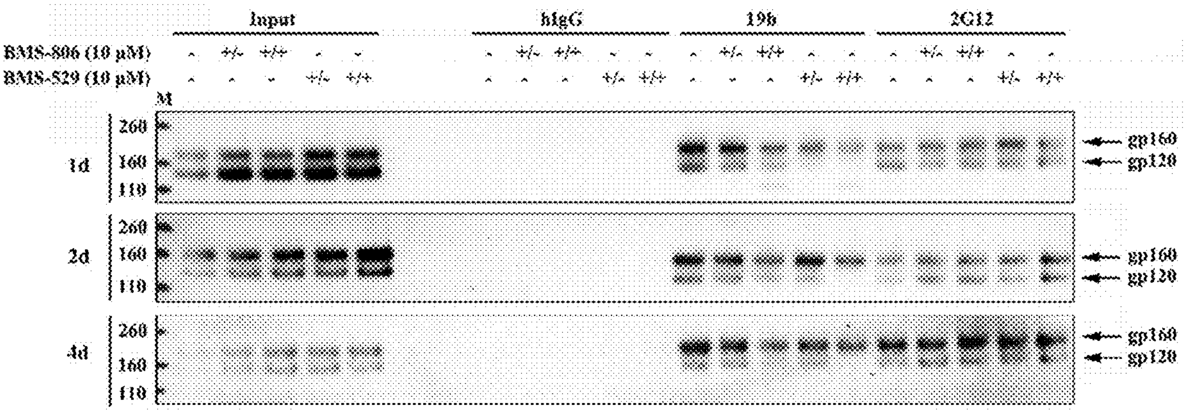
FIG. 4 shows the reversibility of effects on Env for the compounds described herein. VLPs prepared from A549-Gag/Env cells expressing HIV-$1_{AD8}$ Env and Gag-mCherry were incubated with DMSO or 10 μM BMS-806 or BMS-529. The VLPs were pelleted and washed twice, resuspended in PBS with 2% DMSO or fresh compound, and incubated at room temperature for the indicated times. Then the pelleted VLPs were lysed and incubated with antibodies and Protein-A-Sepharose beads. The precipitated proteins were Western blotted with a rabbit anti-gp120 antiserum. The results are shown for the absence of the compound (−), in the continuous presence of the compound (+/+), or after initial exposure to the compound, washing and incubation in PBS with 2% DMSO for the indicated times (+/−).

The BMS-806-induced decrease in binding of the 19b anti-V3 antibody can be used as an indicator of BMS-806-Env binding, allowing estimation of the stability of the Env-compound complex. BMS-806 and BMS-529 were incubated with the HIV-$1_{AD8}$ Env on VLPs. The VLPs were then washed and incubated at room temperature for various lengths of time in a buffer with (+/+) or without (+/−) compound. After this incubation, Env conformation was assessed using the 19b anti-V3 antibody, the 2G12 antibody (the binding of which is not affected by BMS-806), and a negative control human immunoglobulin (hIgG) preparation. 19b recognition of Env in the washed samples (+/−) was compared with those in the samples continuously incubated with the compound (+/+) and the untreated samples (−) (FIG. 4). By twenty-four hours, the conformational effects of BMS-806 on 19b binding were much less evident. The effects of the more potent BMS-529 were still apparent at twenty-four hours, but disappeared by 2-4 days. Despite this slow rate of dissociation of compounds described herein from Env, the binding and the consequent effects of these compounds on Env conformation appear to be reversible.

(vi) The Compounds

In Table 1, recombinant, luciferase-expressing single-round HIV-1 with the indicated HIV-1 Envs or the envelope glycoproteins of the amphotropic murine leukemia virus (AMLV) were incubated with different concentrations of compounds described herein for 30 minutes at 37° C. The virus-compound mixtures were then incubated with Cf2Th-CD4/CCR5 target cells for 48 hours at 37° C. in 5% $CO_2$. Then the cells were lysed and luciferase activity was measured. The 50% inhibitory concentrations ($IC_{50}$ values in nM) were calculated from four independent experiments and are reported as means and standard errors. ND—not determined.

TABLE 1
| Inhibition of HIV-1 infection | | | | |
|---|---|---|---|---|
| | 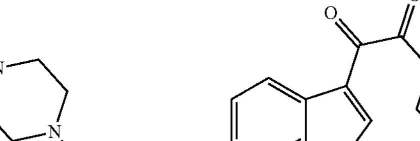<br>AEG-II-159 | 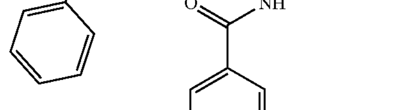<br>AEG-II-168 | 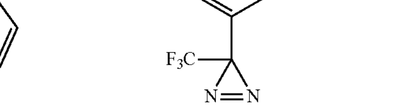<br>AEG-III-032 | 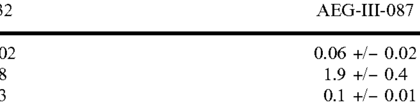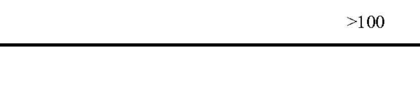<br>AEG-III-087 |
| AD8 | 0.2 +/− 0.05 | 2.8 +/− 0.1 | 0.36 +/− 0.02 | 0.06 +/− 0.02 |
| BG505 | 0.8 +/− 0.05 | 0.22 +/− 0.08 | 1.5 +/− 0.8 | 1.9 +/− 0.4 |
| JR-FL | 1.6 +/− 0.1 | 1.5 +/− 0.2 | 0.6 +/− 0.3 | 0.1 +/− 0.01 |
| JR-FL S375W | >100 | >100 | >100 | >100 |
| AMLV | >100 | >100 | >100 | >100 |

TABLE 1-continued
| Inhibition of HIV-1 infection | | | |
|---|---|---|---|
| | 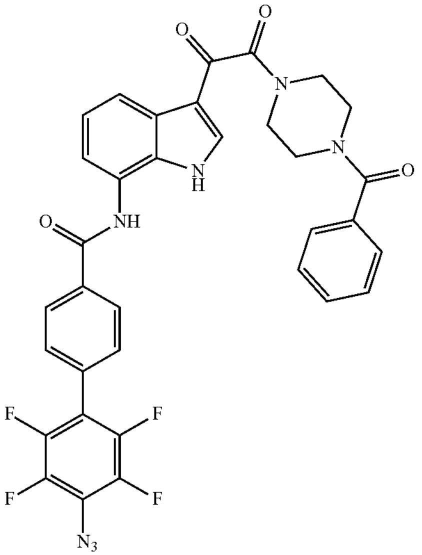 [SMILES: [N-]=[N+]=Nc1c(F)c(F)c(-c2ccc(C(=O)Nc3cccc4c(C(=O)C(=O)N5CCN(C(=O)c6ccccc6)CC5)c[nH]c34)cc2)c(F)c1F] | 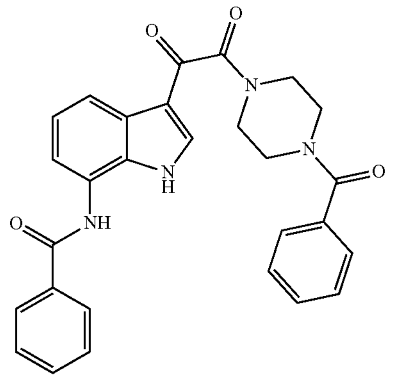 [SMILES: O=C(Nc1cccc2c(C(=O)C(=O)N3CCN(C(=O)c4ccccc4)CC3)c[nH]c12)c1ccccc1] | 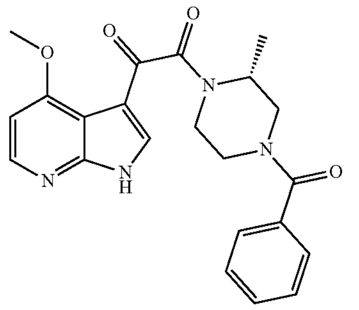 [SMILES: COc1ccnc2[nH]cc(C(=O)C(=O)N3CCN(C(=O)c4ccccc4)C[C@H]3C)c12] |
| | AEG-III-095 | AEG-III-096 | BMS-806 |
| AD8 | 2.2 +/− 0.4 | 2.4 +/− 0.1 | 0.4 +/− 0.01 |
| BG505 | ND | ND | 0.8 +/− 0.2 |
| JR-FL | 0.7 +/− 0.1 | 0.9 +/− 0.1 | 1.6 +/− 0.5 |
| JR-FL S375W | >100 | >100 | >100 |
| AMLV | >100 | >100 | >100 |

Figure 12A:
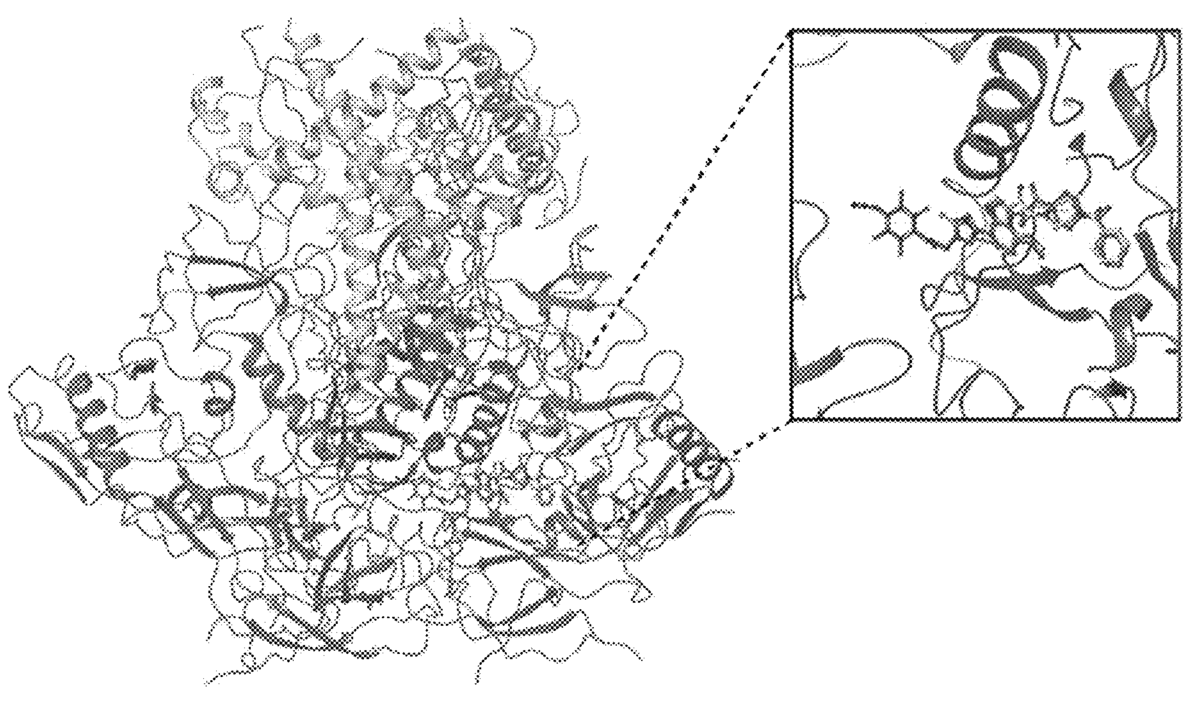
FIGS. 12A-12B show the computational docking of compounds described herein. Maestro and Glide (Schrodinger) were used to dock BMS-529, AEG-II-159, and AEG-II-168 to the HIV-$1_{BG505}$ soluble gp140 SOSIP.664 trimer complexed with BMS-529 (PDB 5U7O). Both AEG compounds docked in the existing BMS-529 pocket in the same orientation as that exhibited by BMS-529 in the crystal structure.
Figure 12B:
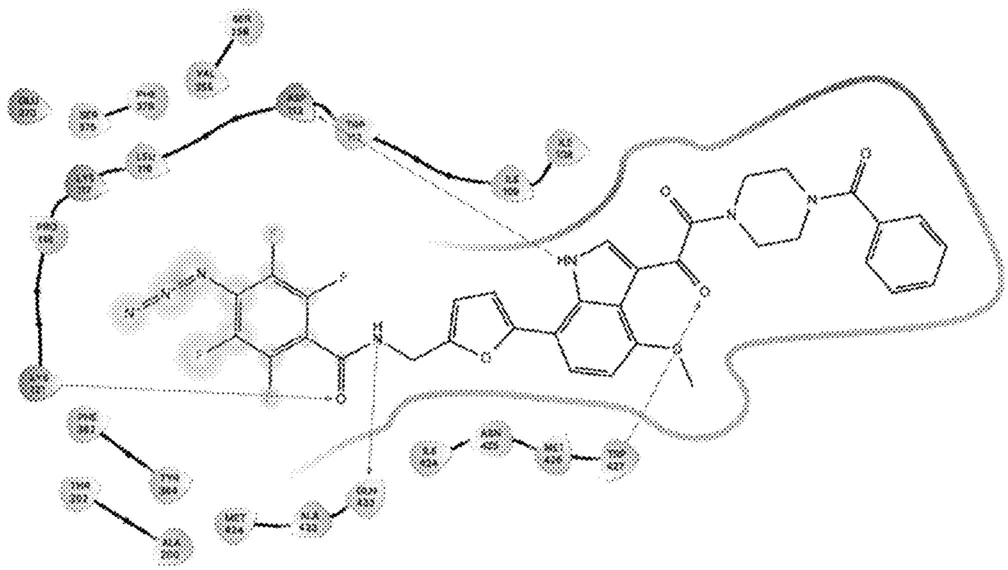

Modeling studies suggested that these photoactivatable groups could be accommodated in complexes of the AEG compounds and soluble gp140 SOSIP.664 Env trimers (PDB 5U7O) and could make additional favorable contacts. Binding energy scores for the best poses of AEG-II-159 and AEG-II-168 were more favorable than that of the cognate docked pose of BMS-529: −13.3 and −14.5 kcal/mol, respectively, versus −12.0 kcal/mol. A representative pose of AEG-II-168 is shown in FIG. 12A and a corresponding interaction map in FIG. 12B. Four compounds inhibited HIV-1 infection with potencies comparable to that of BMS-806 (Table 1). The observed inhibition was completely abolished by the S375W change, which fills the Phe 43 cavity that accommodates the benzoyl ring of compounds. Thus, the antiviral activity of AEG-II-159, AEG-II-168, AEG-III-087 and AEG-III-095 depends upon the availability of the Phe 43 cavity, a gp120 feature also required for BMS-806 and BMS-529 binding.

To determine if the photoactivatable azide or diazirine groups are required for the observed anti-HIV-1 activity of the AEG compounds, compounds lacking these groups (AEG-III-032 and AEG-III-096) were synthesized and tested. AEG-III-032 and AEG-III-096 inhibited HIV-1 infection specifically, with potencies comparable to that of BMS-806 (Table 1).

(a) Effects of the AEG Compounds on Env Conformation

Figure 13A:
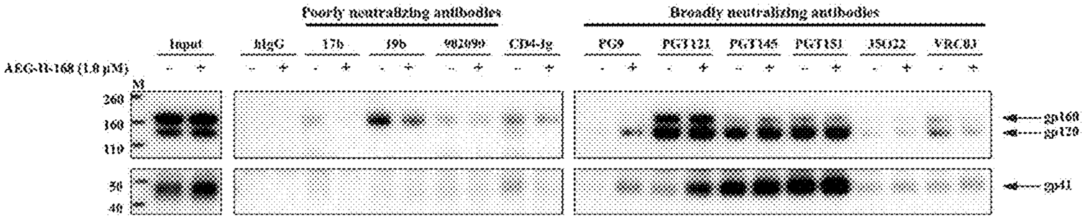
FIGS. 13A-13B show the effect of AEG compounds on the conformation of cell-surface and VLP Env.
Figure 13B:
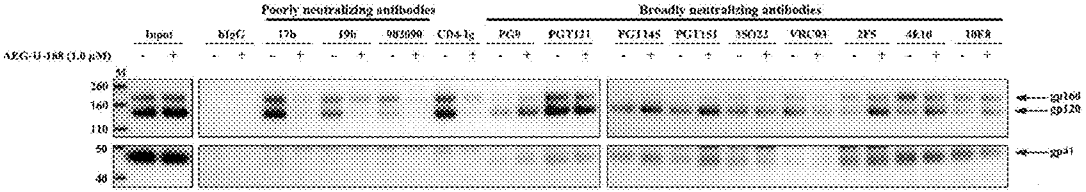
Figure 13C:
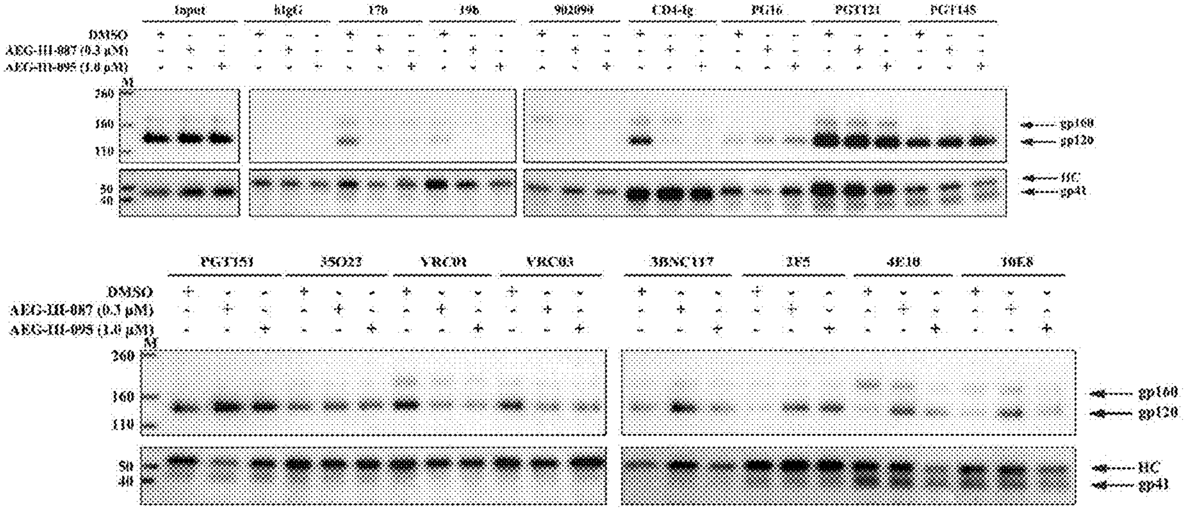

The effects of AEG-II-159, AEG-II-168, AEG-III-087 and AEG-III-095 on HIV-$1_{AD8}$ Env conformation were evaluated. The effects of the AEG compounds on the antigenic profile of the HIV-$1_{AD8}$ Env on cell surfaces or VLPs are shown in FIG. 13. Incubation with the AEG compounds resulted in decreased recognition by poorly neutralizing antibodies, whereas Env recognition by bNAbs was maintained or even increased. One exception was Env recognition by CD4BS bNAbs (VRC01, VRC03), whose binding was moderately decreased by the AEG compounds; although BMS-806 also exhibited a similar effect.

Figure 5:
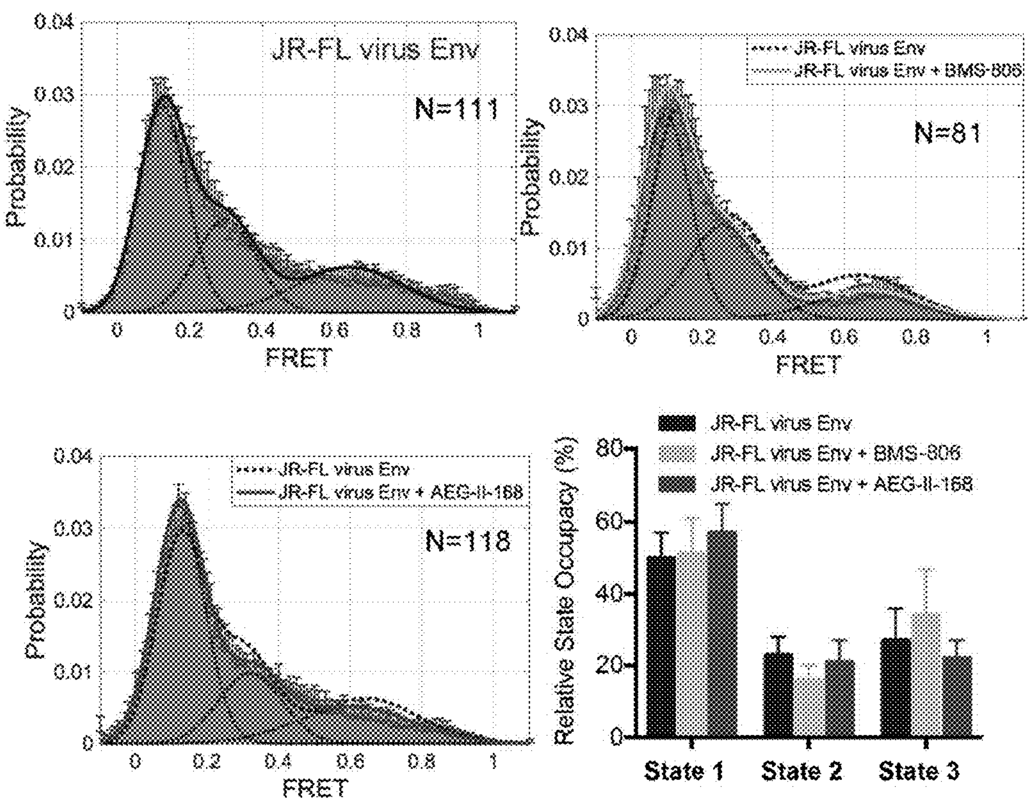
FIG. 5 shows the effect of AEG-II-168 on virion Env conformational states. The indicated number (N) of FRET traces were collected on HIV-$1_{JR-FL}$ virus Env labeled in the gp120 V1 and V4 regions, in the absence and presence of a saturating concentration (100 μM) of BMS-806 or AEG-II-168. FRET histograms were compiled from the data and fitted for three Gaussian distributions centered at a low (0.1) FRET (State 1), intermediate (0.33) FRET (State 3) and high (0.65) FRET (State 2). Relative state occupancies are presented as means+/−standard errors of the mean.

The effects of AEG-II-168 on the conformation of the HIV-$1_{JR-FL}$ Env on virions by smFRET was examined. For these studies, smFRET probes were situated in the gp120 V1 and V4 variable regions and the ratio of labeled to unlabeled Envs was kept low so that a single protomer of the Env trimer could be evaluated. In the presence of saturating concentrations of AEG-II-168, the HIV-$1_{JR-FL}$ virion Env maintained a State-1-dominant conformation (FIG. 5).

(b) Effect of AEG Compounds on Gp120 Association with the Env Trimer

Figure 6A:
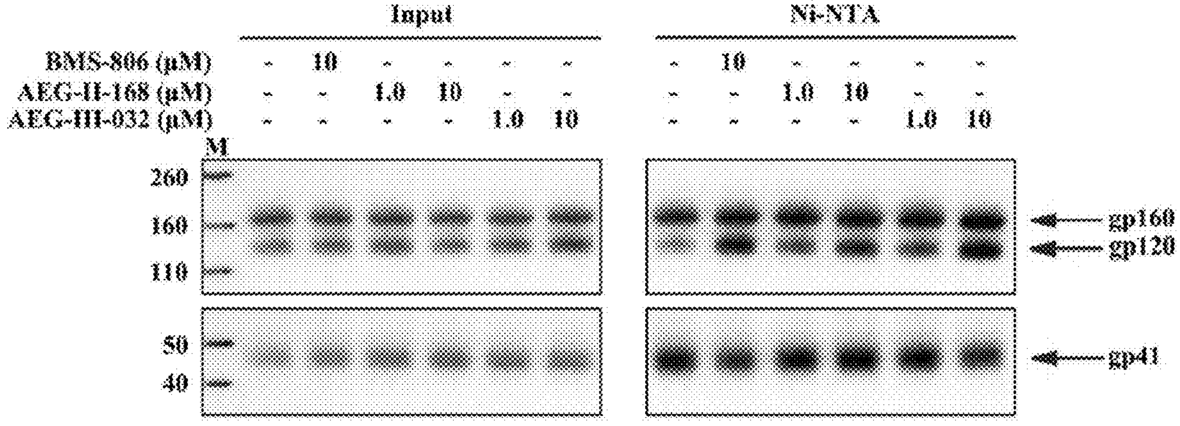
FIGS. 6A-6B show the effect of AEG compounds on gp120 association with solubilized Env complexes. In these figures, Triton X-100 lysates of A549-Env cells expressing HIV-$1_{AD8}$ Env were incubated with Ni-NTA beads in the presence of the indicated compounds. The precipitated Envs were analyzed by Western blotting with a rabbit anti-gp120 antibody (upper panels) and the 4E10 anti-gp41 antibody (lower panels). The results of single experiments are shown; the experiments were repeated with similar results.
Figure 6B:
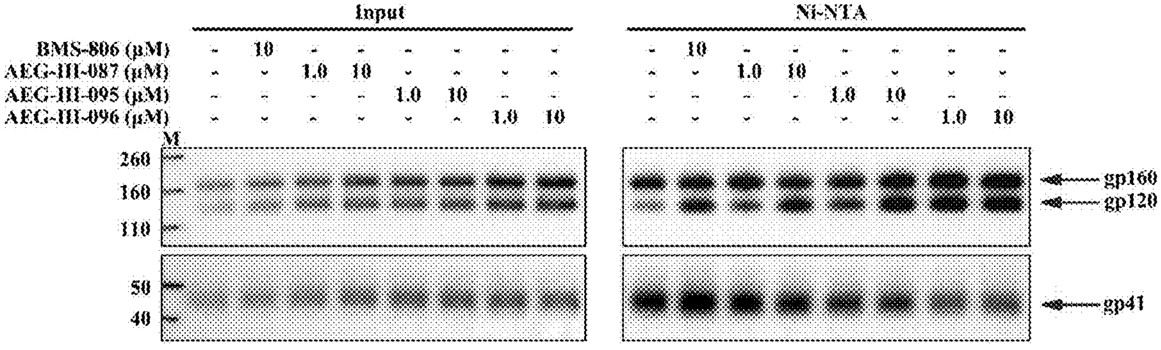

All four photoactivatable AEG compounds, as well as AEG-III-032 and AEG-III-096 lacking photoactivatable groups, stabilized the association of gp120 with detergent-solubilized Env trimers (FIG. 6).

Figure 7A:
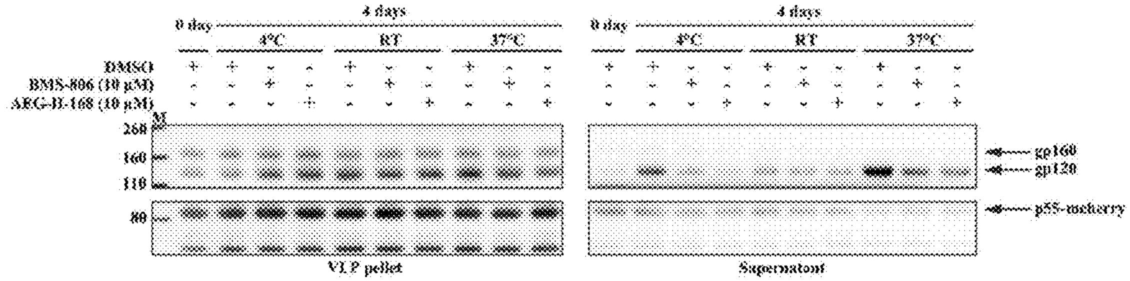
FIGS. 7A-7B show the effect of BMS-806 and AEG compounds on gp120 shedding from VLPs. In both figures, VLPs with the HIV-$1_{AD8}$ Env were incubated with DMSO, BMS-806 or AEG compounds in physiologic buffer for 4 days at 4° C., room temperature (RT) or 37° C. The VLPs were then pelleted and lysed; the lysed VLPs and supernatants were analyzed by Western blotting with a rabbit anti-gp120 antibody (upper panels) and anti-Gag p55/p24/p17 antibody (lower panels). Note that, because the amount of shed gp120 is low compared with that of the VLP-associated gp120, the level of gp120 in the VLP supernatants is a more accurate indicator of gp120 shedding. The results of typical experiments of two independent experiments are shown.
Figure 7B:
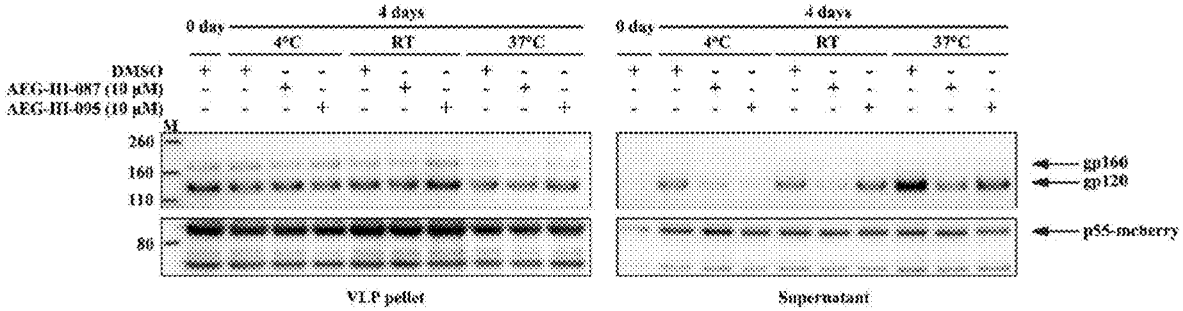

The effect of BMS-806 and compounds described herein on the spontaneous shedding of gp120 from HIV-$1_{AD8}$ VLPs was examined at 4° C., 20° C. and 37° C. in the absence of detergent. BMS-806, AEG-II-168, AEG-III-087 and AEG-III-095 decreased the shedding of gp120 into the VLP supernatant at 4° C. and 37° C. (FIG. 7). Thus, these compounds may stabilize the interaction of gp120 with the native membrane Env trimer under physiologic conditions.

(c) Long-Term Effects of AEG Compounds on Env Conformation

Figure 8A:
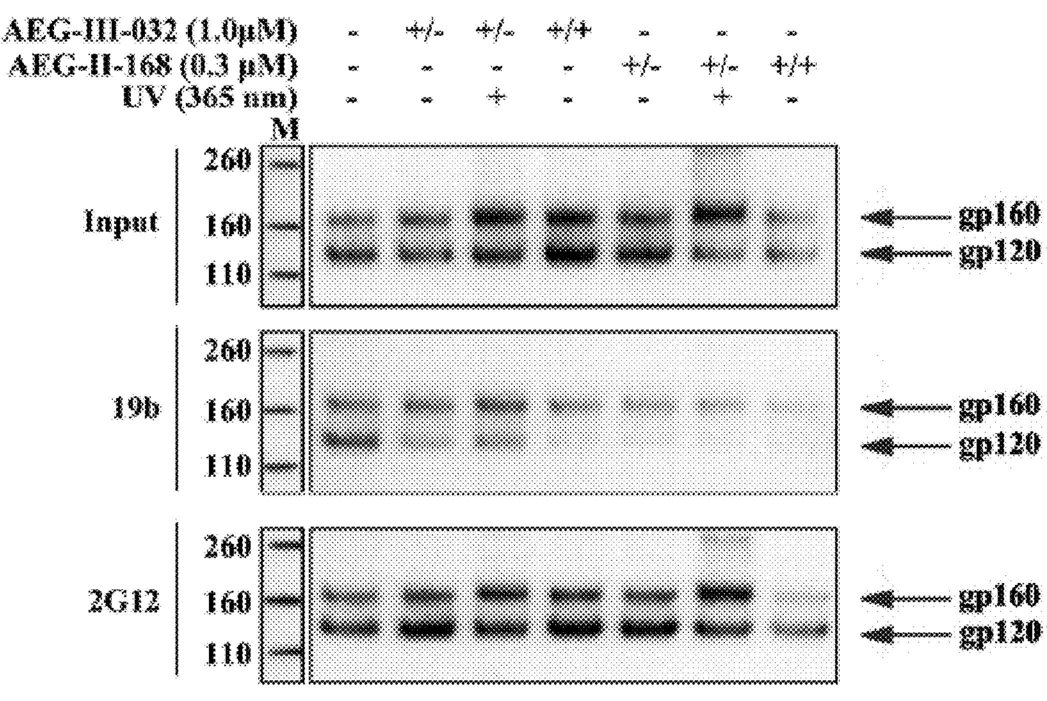
FIGS. 8A-8B show the duration of the effect of AEG compounds on Env conformation. In both figures, VLPs prepared from A549-Gag/Env cells expressing HIV-$1_{AD8}$ Env were incubated with DMSO or the indicated AEG compound and, in some cases, irradiated with ultraviolet light (UV). The pelleted VLPs were washed twice and then resuspended in PBS with 2% DMSO or fresh compound at room temperature for one week. Then the VLPs were pelleted and lysed. The VLP lysates were directly Western blotted (Input) or incubated with the 19b or 2G12 antibody and Protein A-Sepharose beads. The precipitated proteins were Western blotted with a rabbit anti-gp120 antiserum. The results are shown for the absence of the compound (−), in the continuous presence of the compound (+/+), or after initial exposure to the compound, washing and incubation in PBS with 2% DMSO for one week (+/−). The results of typical experiments of three independent experiments are shown.
Figure 8B:
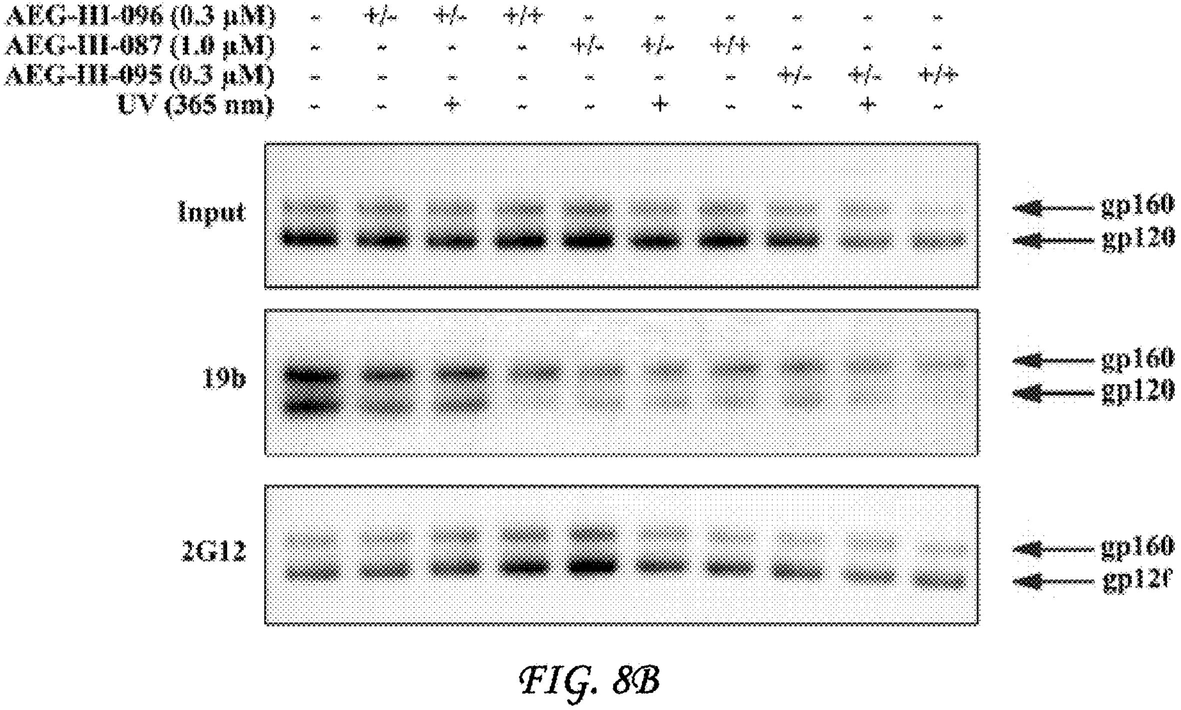
Figure 14:
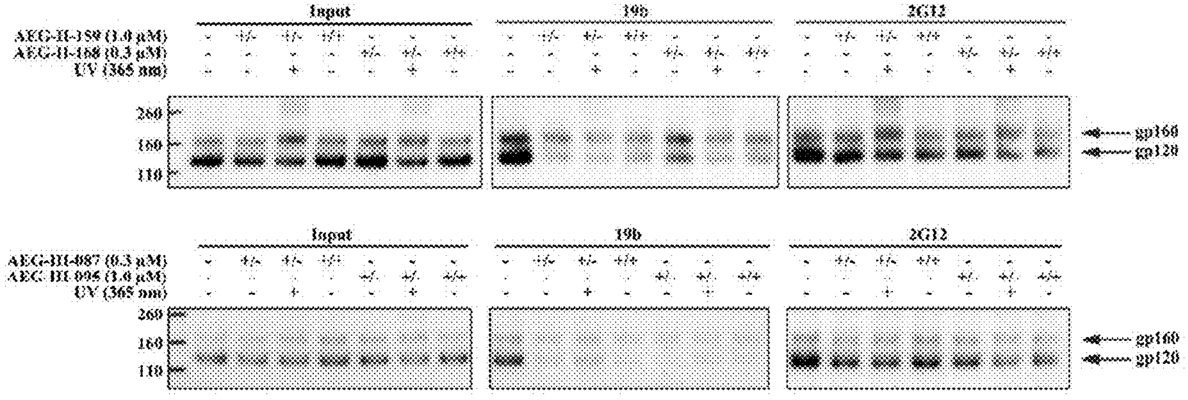
FIG. 14 shows the duration of the effect of AEG compounds on VLP Env conformation. VLPs with the HIV-$1_{AD8}$ Env were incubated with DMSO or the indicated AEG compound and, in some cases, irradiated with UV light. The VLPs were pelleted and washed twice and then resuspended in either PBS with 2% DMSO or fresh compound at room temperature for 3 weeks. The VLPs were then pelleted, lysed and processed as described in the FIG. 8 legend. Results are shown for the absence of the compound (−), continuous presence of the compound (+/+), or after initial exposure to the compound, washing and incubation in PBS with 2% DMSO for 3 weeks (+/−).
Figure 15:
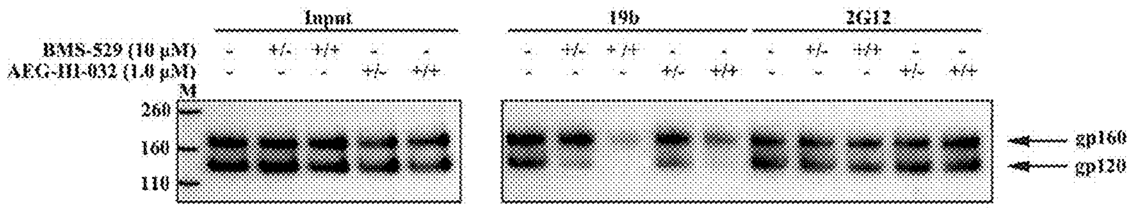
FIG. 15 shows the reversibility of effects on VLP Env conformation for compounds described herein. VLPs with the HIV-$1_{AD8}$ Env were incubated with DMSO, BMS-529 or AEG-III-032. The VLPs were pelleted and washed twice, and then resuspended in either PBS with 2% DMSO or fresh compound at room temperature for 7 days. The VLPs were then pelleted, lysed and processed as described in the FIG. 8 legend. Results are shown for the absence of the compound (−), continuous presence of the compound (+/+), or after initial exposure to the compound, washing and incubation in PBS with 2% DMSO for 7 days (+/−).

The decrease in 19b antibody recognition was used to evaluate the stability of the association of the AEG compounds with HIV-$1_{AD8}$ Env on VLPs. Surprisingly, even without ultraviolet (UV) irradiation, the effects of AEG-II-159, AEG-II-168, AEG-III-087 and AEG-III-095 on 19b recognition persisted for at least 3 weeks after washing (FIGS. 8 and 14). AEG-III-032, which lacks a photoactivatable group, was tested and it was found that the effects of this control compound on Env conformation were reversed by 7 days following removal of the VLPs from the compound solution (FIGS. 8 and 15). Likewise, AEG-III-096, a compound lacking a photoactivatable group, exhibited much faster reversibility than the corresponding compounds (AEG-III-087 and AEG-III-095) with diazirine and azide groups, respectively (FIG. 8). Apparently, the durability of the effects of AEG-II-159, AEG-II-168, AEG-III-087 and AEG-III-095 on HIV-1 Env conformation is enhanced by the presence of the photoactivatable groups, but is not dependent on UV crosslinking.

Figure 9A:
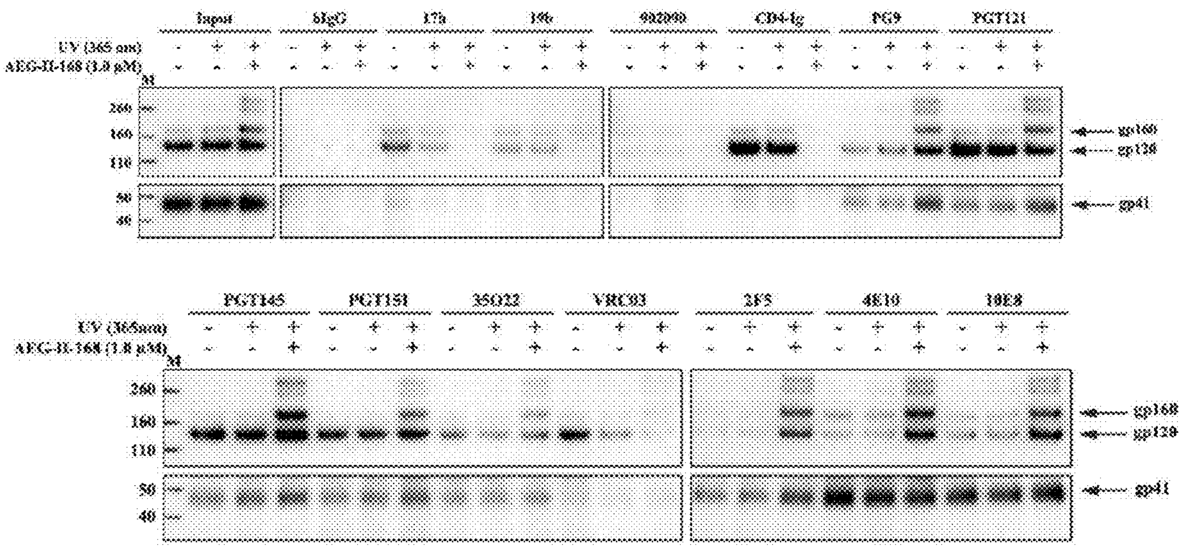
FIGS. 9A-9B show the long-term effects of AEG compounds on HIV-1 Env conformation. In both figures, VLPs prepared from A549 cells expressing HIV-$1_{AD8}$ Env were incubated with DMSO or the indicated AEG compound and, in some cases, irradiated with UV light. The pelleted VLPs were washed and then resuspended in PBS with 2% DMSO. The VLPs were incubated at room temperature for 2 weeks. The VLPs were pelleted and lysed, and the cell lysates were incubated with the indicated antibodies and Protein A-Sepharose. The precipitated proteins were Western blotted with a rabbit anti-gp120 antiserum (upper panels) and with the 4E10 anti-gp41 antibody (lower panels). The results of typical experiments of two independent experiments are shown.
Figure 9B:
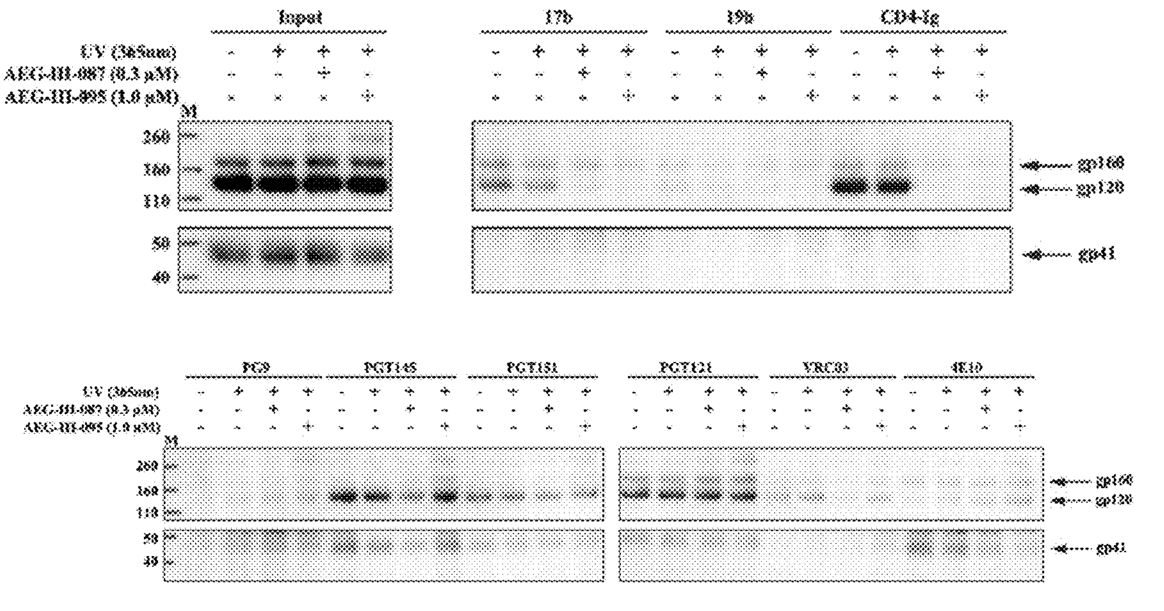

The compounds described herein potentially could be used to stabilize a State-1 conformation in Env immunogens. The antigenic profile of HIV-$1_{AD8}$ Env in VLPs was compared two weeks after each of the following treatments: buffer/DMSO, UV irradiation, and AEG compounds (AEG-II-168, AEG-III-087 and AEG-III-095) plus UV irradiation. Following these treatments, the VLPs were pelleted, washed and resuspended in buffer without compound at 4° C. for two weeks, at which time a panel of antibodies was used to evaluate the Env conformation. All three AEG compounds lowered Env recognition by poorly neutralizing antibodies and, with the exception of the CD4BS antibodies, maintained the integrity of the bNAb epitopes (FIGS. 9A and 9B). Treatment of the VLPs with AEG-II-168 and UV irradiation resulted in increased recognition by several bNAbs (PG9, PGT145, PGT151, 35022, 2F5, 4E10 and 10E8); this increase was not seen for AEG-III-087 or AEG-III-095. UV irradiation of VLP Env in the presence of AEG-II-168 also led to an intensification of the gp160 band and the appearance of two new bands of approximately 240 and 280 kD. It is speculated that these represent gp120-gp41, gp120-gp120 and gp120-gp120-gp41 crosslinked products, respectively; the long extension (furan ring-amide linkage-tetrafluorobenzene ring) between the gp120-docking portion and the photoactivable azide of AEG-II-168 apparently allows these crosslinks more than in AEG-III-087 and AEG-III-095, which have shorter spacers. In summary, the above results indicate that several of the AEG compounds can exert long-term stabilizing effects on State-1-like Env conformations.

B. Discussion

In cells expressing HIV-1 Envs, both mature (cleaved) and uncleaved Envs are transported to the cell surface. The mature, functional Env, which largely resides in a State-1 conformation, is able to be recognized by most bNAbs but not by poorly neutralizing antibodies. In general, it was found that the binding of most bNAbs to the mature Env trimer is maintained or increased in the presence of BMS-806, whereas BMS-806 inhibits the binding of poorly neutralizing antibodies to the uncleaved Env. The effects of BMS-806 on the antigenicities of the cleaved cell-surface Env and the cleaved VLP Env strongly correlated. The differential effects of BMS-806 on the binding of bNAbs and poorly neutralizing antibodies are consistent with the compound stabilizing a State-1-like, pre-triggered conformation of the membrane Env trimer.

It was found that BMS-806 and compounds described herein strengthened gp120:Env association on the viral surface under physiologic conditions, as well as in detergent lysates. BMS-806-induced enrichment of a pretriggered, State-1-like Env conformation and the consequent decrease of open State-3 Env conformations likely relates to the observed stabilization of gp120:trimer association.

It also was observed that BMS-806 enhances Env recognition by V2 quaternary antibodies. Although BMS-806 did not impede the decrease in Env recognition by V2 quaternary antibodies that accompanies CD4 binding, BMS-806 can apparently decrease the spontaneous sampling of more open State 2/3 Env conformations; the blockade of spontaneous transitions is presumably more readily achieved by a small molecule than the blockade of the changes in the gp120 trimer association domain induced by a large protein like CD4.

The assays measuring the reversibility of Env conformational effects of compounds described herein indicate a remarkably slow off-rate of these compounds. Even the parental compounds, BMS-806 and BMS-529, as well as the control compounds, AEG-III-032 and AEG-III-096, which lack photoactivatable groups, required 1-4 days to reverse their conformational effects on Env. Insertion of these compounds into a conserved, hydrophobic interdomain interface on Env may impose unfavorable enthalpic and entropic penalties on their extraction from Env and resolubilization. The addition of photoactivatable groups in AEG-II-159 and AEG-II-168 significantly decreased their reversibility, with maintenance of Env conformational effects for at least three weeks. Surprisingly, even without UV irradiation and even when exposure to visible light was minimized, this prolongation of Env conformational effect was observed.

The availability of compounds that can maintain State-1-like Env conformations for prolonged time periods may assist presentation of this conformation to the immune system. Given that State 1 is targeted by many bNAbs and is intrinsically metastable, limiting the conformations of Env immunogens to State 1 may facilitate the elicitation of bNAbs. Compounds with prolonged activity may also assist structural studies of State-1-like conformations, which could benefit from the availability of Env trimer preparations that are enriched in these pre-triggered conformations.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A compound of Formula (I):

(I)

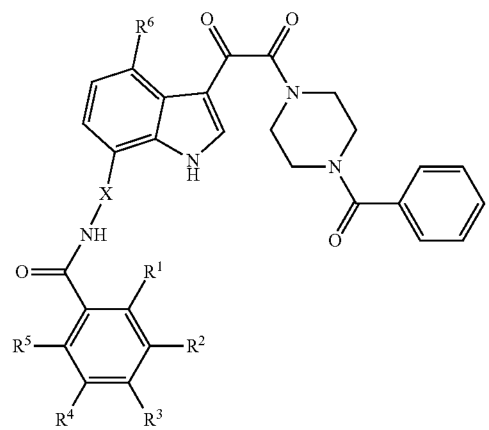

wherein:

(i) $R^1$ to $R^5$ are halo, or (ii) $R^1$ to $R^5$ are H or optionally substituted diazirinyl, provided that one of $R^1$ to $R^5$ is optionally substituted diazirinyl, or (iii) four of $R^1$ to $R^5$ are halo and one of $R^1$ to $R^5$ is $N_3$;

$R^6$ is H, $C_{1-6}$alkyl, or $C_{1-6}$alkoxy; and

X is absent, -furanyl-, or furanyl-$C_{1-6}$alk-;

or a pharmaceutically acceptable salt thereof.

2. The compound of claim 1, that is a compound of formula (IA) or (IB):

(IA)

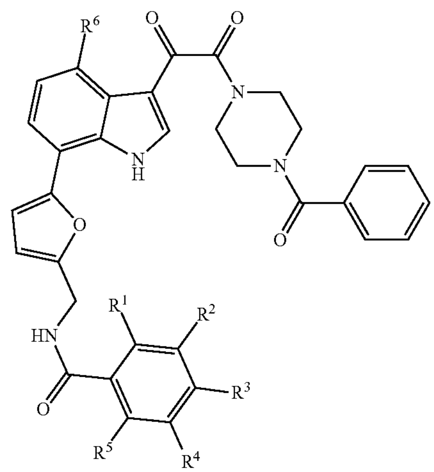

-continued (IB)

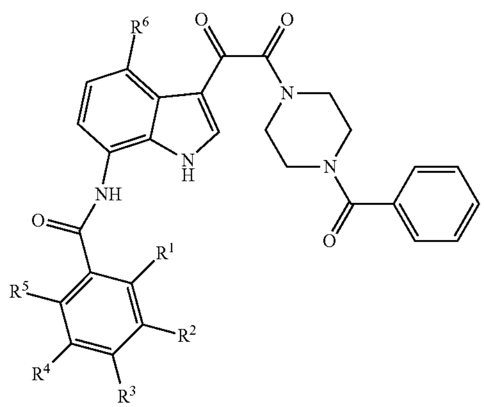

or a pharmaceutically acceptable salt thereof.

3. A compound of Formula (I):

(I)

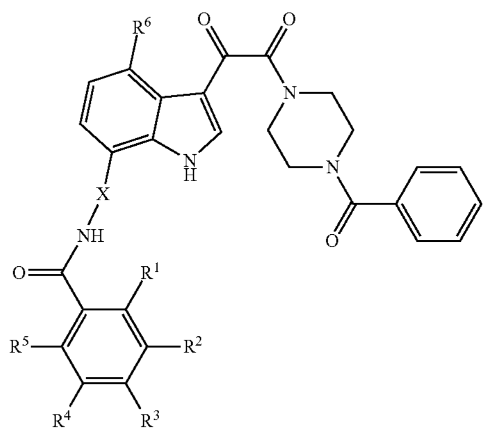

wherein:

$R^1$ to $R^5$ are, independently, H, halo, optionally substituted $C_{1-6}$alkyl, optionally substituted diazirinyl, or $N_3$;

$R^6$ is $C_{1-6}$alkoxy; and

X is absent,-furanyl-, or furanyl-$C_{1-6}$alk-;

or a pharmaceutically acceptable salt thereof.

4. The compound of claim 1, wherein $R^1$ to $R^5$ are halo.

5. The compound of claim 1, wherein four of $R^1$ to $R^5$ are halo and one of $R^1$ to $R^5$ is $N_3$.

6. The compound of claim 1, wherein $R^1$, $R^2$, $R^4$, and $R^5$ are halo and $R^3$ is $N_3$.

7. The compound of claim 1, wherein the halo is F, Cl, or Br.

8. The compound of claim 3, wherein $R^1$ to $R^5$ are H.

9. The compound of claim 1, wherein one of $R^1$ to $R^5$ is optionally substituted diazirinyl.

10. The compound of claim 1, wherein the diazirinyl is optionally substituted with halo, $C_{1-6}$alkyl, or $C_{1-6}$haloalkyl.

11. The compound of claim 1, wherein the diazirinyl is optionally substituted with $C_{1-6}$haloalkyl.

12. The compound of claim 1, wherein the diazirinyl is

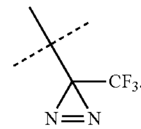

13. The compound of claim 1, wherein $R^6$ is H.

14. The compound of claim 3, wherein $R^1$ to $R^5$ are, independently, H, halo, optionally substituted diazirinyl, or $N_3$.

15. A compound of Formula (I):

(I)

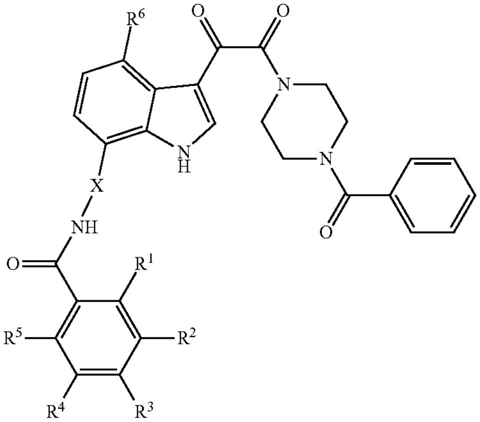

wherein:

$R^1$ to $R^5$ are, independently, H, halo, optionally substituted $C_{1-6}$alkyl, optionally substituted diazirinyl, or $N_3$;

$R^6$ is $C_{1-6}$alkyl; and

X is absent, -furanyl-, or furanyl-$C_{1-6}$alk-;

or a pharmaceutically acceptable salt thereof.

16. The compound of claim 1, wherein X is absent.

17. A compound of Formula (I):

(I)

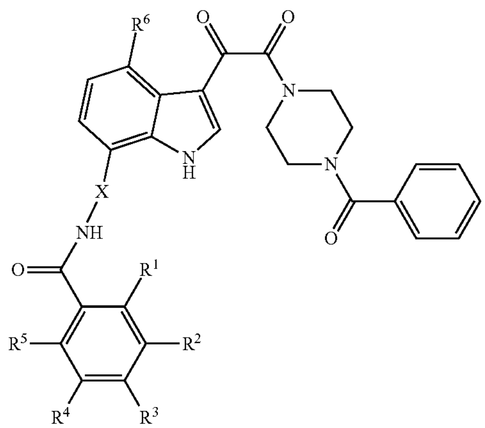

wherein:

$R^1$ to $R^5$ are, independently, H, halo, optionally substituted $C_{1-6}$alkyl, optionally substituted diazirinyl, or $N_3$;

$R^6$ is H, $C_{1-6}$alkyl, or $C_{1-6}$alkoxy; and

X is furanyl or furanyl-$C_{1-6}$alk;

or a pharmaceutically acceptable salt thereof.

18. The compound of claim 1, wherein X is furanyl-$C_{1-6}$alk.

19. A compound selected from the group consisting of:

AEG-II-159

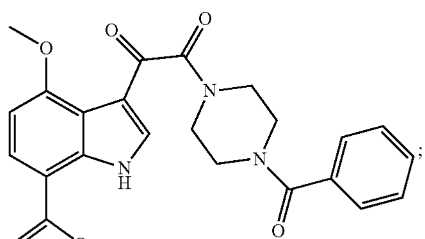

;

AEG-II-168

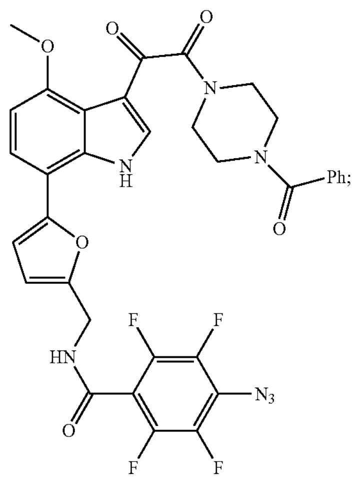

;

AEG-III-032

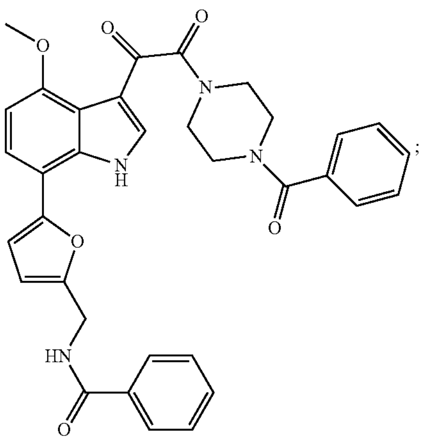

;

-continued

AEG-III-087

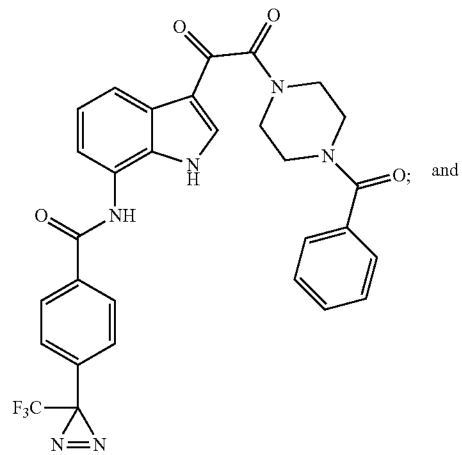

; and

AEG-III-095

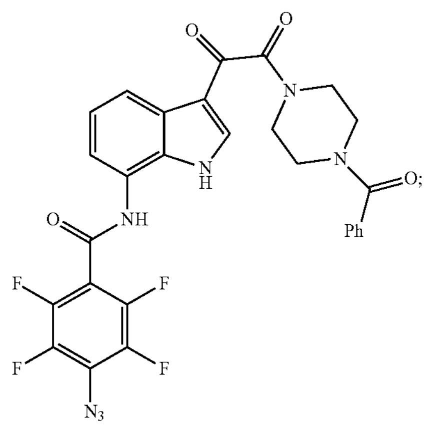

;

or a pharmaceutically acceptable salt thereof.

20. A pharmaceutical composition comprising the compound of claim 1.

21. A method for treating human immunodeficiency virus (HIV) or stabilizing the state-1 conformation of HIV-1 envelope glycoproteins in a subject in need thereof, comprising administering the compound of claim 1 to the subject in need thereof.

22. The method of claim 21, wherein the HIV is HIV-1.

23. A method for treating human immunodeficiency virus (HIV) or stabilizing the state-1 conformation of HIV-1 envelope glycoproteins in a subject in need thereof, comprising administering the compound of claim 3 to the subject in need thereof.

24. A method for treating human immunodeficiency virus (HIV) or stabilizing the state-1 conformation of HIV-1 envelope glycoproteins in a subject in need thereof, comprising administering the compound of claim 15 to the subject in need thereof.

25. A method for treating human immunodeficiency virus (HIV) or stabilizing the state-1 conformation of HIV-1 envelope glycoproteins in a subject in need thereof, comprising administering the compound of claim 17 to the subject in need thereof.

26. A method for treating human immunodeficiency virus (HIV) or stabilizing the state-1 conformation of HIV-1 envelope glycoproteins in a subject in need thereof, comprising administering the compound of claim 19 to the subject in need thereof.

* * * * *